(12) United States Patent (10) Patent No.: US 9,357,920 B2
Yates et al. (45) Date of Patent: Jun. 7, 2016

(54) HAND-HELD PORTABLE FUNDUS CAMERA FOR SCREENING PHOTOGRAPHY

(75) Inventors: Paul Andrew Yates, Charlottesville, VA (US); Kenneth Tran, Burke, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1026 days.

(21) Appl. No.: 13/394,055

(22) PCT Filed: Sep. 3, 2010

(86) PCT No.: PCT/US2010/047909
§ 371 (c)(1),
(2), (4) Date: May 21, 2012

(87) PCT Pub. No.: WO2011/029064
PCT Pub. Date: Mar. 10, 2011

(65) Prior Publication Data
US 2012/0229617 A1 Sep. 13, 2012

Related U.S. Application Data

(60) Provisional application No. 61/240,027, filed on Sep. 4, 2009, provisional application No. 61/372,270, filed on Aug. 10, 2010.

(51) Int. Cl.
*A61B 3/15* (2006.01)
*A61B 3/12* (2006.01)
*G06K 9/00* (2006.01)

(52) U.S. Cl.
CPC . *A61B 3/156* (2013.01); *A61B 3/12* (2013.01); *G06K 9/00604* (2013.01)

(58) Field of Classification Search
None
See application file for complete search history.

(56) References Cited

U.S. PATENT DOCUMENTS 4,257,688 A 3/1981 Matsumura
4,266,861 A 5/1981 Sawa
(Continued)

FOREIGN PATENT DOCUMENTS

EP 1354551 A1 10/2003
WO WO-2006013579 A1 2/2006
(Continued)

OTHER PUBLICATIONS

Chalam, K V, et al., "Evaluation of modified portable digital camera for screening of diabetic retinopathy", Ophthalmic Res 42(1), (2009), 60-62.

*Primary Examiner* — Geepy Pe
*Assistant Examiner* — William Adrovel
(74) *Attorney, Agent, or Firm* — Schwegman Lundberg & Woessner, P.A.

(57) ABSTRACT

System and Method pertaining to the modification and integration of an existing consumer digital camera, for example, with an optical imaging module to enable point and shoot fundus photography of the eye. The auto-focus macro capability of existing consumer cameras is adapted to photograph the retina over an extended diopter range, eliminating the need for manual diopter focus adjustment. The thru-the-lens (TTL) auto-exposure flash capability of existing consumer cameras is adapted to photograph the retina with automatic flash exposure eliminating the need for manual flash adjustment. The consumer camera imaging sensor and flash are modified to allow the camera sensor to perform both non-mydriatic focusing of the retina using infrared illumination and standard color flash photography of the retina without the need for additional imaging sensors or mechanical filters. These modifications and integration of existing consumer cameras for fundus photography of the eye significantly improve ease of manufacture and usability over existing fundus cameras.

188 Claims, 17 Drawing Sheets

(56) References Cited

U.S. PATENT DOCUMENTS

| | | |
|---|---|---|
| 5,543,865 A | 8/1996 | Nanjo |
| 5,668,865 A | 9/1997 | Duttweiler et al. |
| 5,764,341 A | 6/1998 | Fujieda et al. |
| 6,546,198 B2 | 4/2003 | Ohtsuka |
| 7,048,379 B2 | 5/2006 | Miller et al. |
| 7,118,218 B2 | 10/2006 | Barker |
| 7,364,297 B2 | 4/2008 | Goldfain et al. |
| 7,481,534 B2 | 1/2009 | Fink |
| 2002/0061190 A1* | 5/2002 | Kawasaki et al. ............ 396/157 |
| 2003/0114733 A1* | 6/2003 | Farrell et al. ................. 600/167 |
| 2003/0206272 A1* | 11/2003 | Cornsweet et al. ........... 351/206 |
| 2004/0263784 A1* | 12/2004 | Cornsweet et al. ........... 351/221 |
| 2005/0041207 A1* | 2/2005 | Miller et al. .................. 351/200 |
| 2005/0117118 A1* | 6/2005 | Miller et al. .................. 351/246 |
| 2006/0146284 A1* | 7/2006 | Collins et al. ................ 351/215 |
| 2007/0019156 A1* | 1/2007 | Fink .............................. 351/200 |
| 2008/0100801 A1* | 5/2008 | Yahagi et al. ................ 351/206 |
| 2008/0218695 A1* | 9/2008 | Obrebski ...................... 351/213 |
| 2008/0231803 A1* | 9/2008 | Feldon et al. ................ 351/206 |
| 2009/0201467 A1 | 8/2009 | Smith et al. |
| 2009/0261944 A1* | 10/2009 | Fukuta et al. ................. 340/5.8 |

FOREIGN PATENT DOCUMENTS

| | | |
|---|---|---|
| WO | WO-2006086269 A2 | 8/2006 |
| WO | WO-2009098516 A2 | 8/2009 |
| WO | WO-2010129775 A1 | 5/2010 |

\* cited by examiner

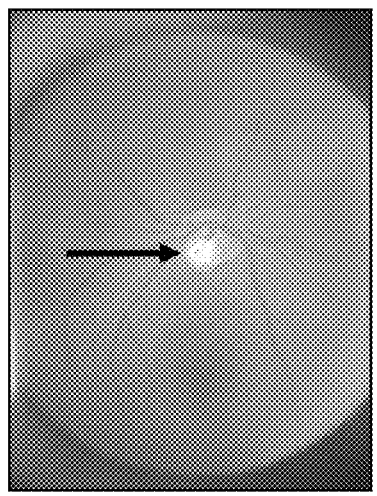
FIG. 12B
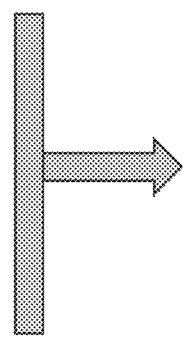
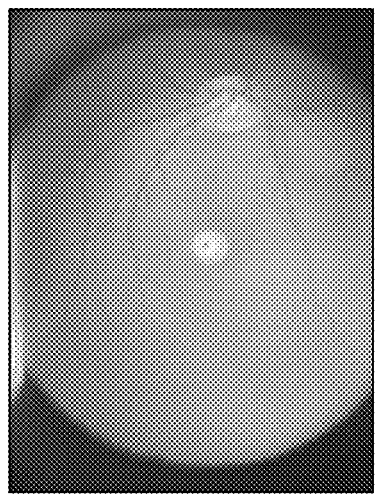
FIG. 12A
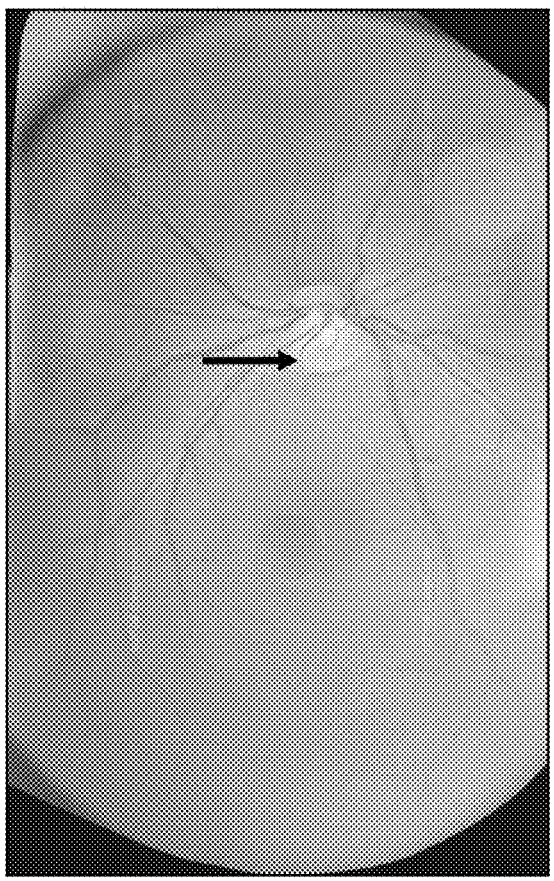
FIG. 12C

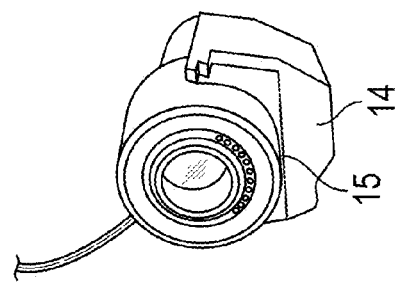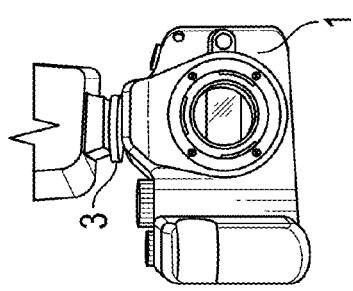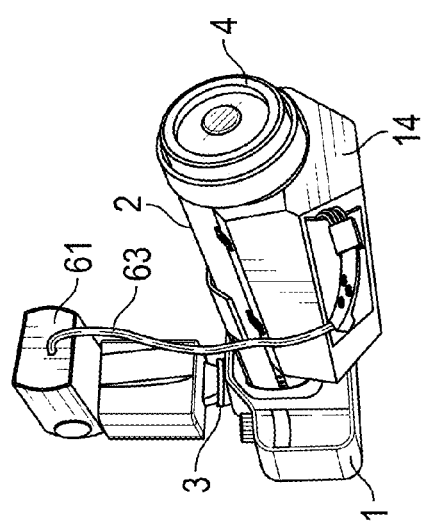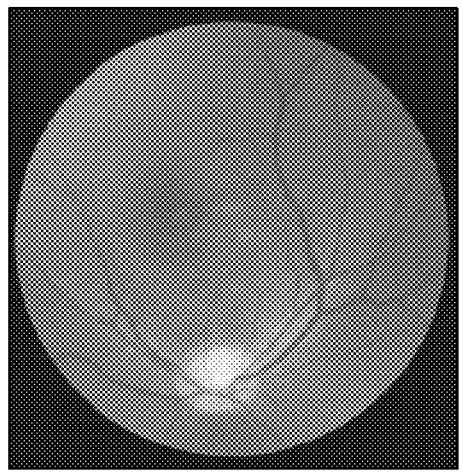
FIG. 15A
FIG. 15B
FIG. 15C

HAND-HELD PORTABLE FUNDUS CAMERA FOR SCREENING PHOTOGRAPHY

RELATED APPLICATIONS

The present application is a U.S. National Stage filing under 35 U.S.C. 371 from International Patent Serial No. PCT/US2010/047909, filed Sep. 3, 2010 and published on Mar. 10, 2011 as WO 2011/029064 A1, which claims priority from U.S. Provisional Application Ser. No. 61/240,027, filed Sep. 4, 2009, entitled "Hand-Held Portable Fundus Camera and Related Method thereof" and U.S. Provisional Application Ser. No. 61/372,270, filed Aug. 10, 2010, entitled "Hand-Held Portable Fundus Camera and Related Method thereof;" the disclosures of which are hereby incorporated by reference herein in their entirety.

FIELD OF THE INVENTION

The present invention relates to a fundus camera for photographing the fundus of an eye and more particularly to a portable fundus camera in which additional optics and illumination are fully integrated with an existing consumer camera device to enable the consumer camera device to perform point and shoot photography the retina. The enhancement of capabilities of the existing consumer camera device enable a fundus camera with overall lower complexity, higher degree of integration, improved ease of manufacturing, automatic focusing and automatic image exposure for retina screening photography as compared to existing and proposed fundus camera devices.

BACKGROUND OF THE INVENTION

Diabetic Retinopathy (DR) is an eye disease affecting millions of patients with type I and type II diabetes. 45% of Americans diagnosed with diabetes have some form of DR, and nearly all patients who have type I diabetes for more than 20 years will show signs of DR. In the US, DR is responsible for almost 8% of legal blindness and is the leading cause of new cases of blindness in adults of 20-74 years of age. In addition, the presence of DR is growing at a dramatic rate in developing countries as the number of type II diabetics increases. In India, diabetic retinopathy has jumped from $17^{th}$ to the sixth leading cause of blindness within twenty years. Similar increases can be seen worldwide and has become a key concern for the World Health Organization.

With close monitoring and annual eye exams, diabetic retinopathy can be diagnosed and successfully treated. According to the American Academy of Ophthalmology (AAO), 95 percent of diabetics with DR can avoid vision loss if treated on time. For this reason, a yearly dilated screening exam is currently recommended by the AAO for all diabetic patients. Traditionally dilated screening exams have required referral to eye care specialists because patient's primary care facilities lack the necessary tools and staff to properly diagnose DR. Due to the inconvenience and extra cost associated with seeing a specialist, patients often fail to follow up on their referral.

Over the last two decades, multiple attempts have been made to address these barriers to screening involving placement of a camera for retina photography within the primary care physician's office. These efforts have largely been hampered by difficult to use and expensive retinal diagnostic devices costing upward of $50,000. Retina camera cost has remained high due to the inherently demanding optical and illumination design that requires complex manufacturing processes. Usability and cost of the devices have similarly been limited by the need to implement a custom image recording device to accurately record images formed by these complex optical designs. These custom image recording devices usually require multiple image sensors and image display units for initial image alignment/focusing and actual final image acquisition. Further, they often require manual control of focusing, image exposure, and white balance, to achieve acceptable final image acquisition, limiting their use to skilled practitioners of ophthalmic photography.

A standard consumer camera device such as a "point and shoot" or DSLR camera does not have an inherent capability to perform fundus photography given the complex optics and illumination required to form an image of the retina. In most existing fundus cameras, the device forms a donut of illumination measuring approximately 3 mm to 7 mm that is focused on the patient's eye. This donut of light is formed by the fundus camera itself through a series of optics and built in illumination source. Alternatively, off axis non-donut illumination can be used and is the basis of indirect ophthalmoscopy. This approach is not commonly employed commercially as photographic quality is impacted negatively by this technique, in particular with respect to evenness of the field illumination as compared to donut illumination. Condensing lenses are required to form an image of the retina that is created by the reflection of light off the back of the eye in response to the donut illumination. Most cameras then employ a separate optics stage to focus the retinal image produced by the condensing lens onto a CCD or CMOS image sensor either built into or externally attached to the device (e.g., a consumer camera device digital camera back which consists of the DSLR body with image sensor alone without the detachable front DSLR camera lens on it). Even when a digital camera back is used, this approach has significant limitations in that auto-focus, auto-exposure, auto-white balance capabilities of the consumer camera device are no longer available. Finally, non-mydriatic fundus photography, in which the patient does not require prior pharmacologic dilation, is commonly used in screening photography and relies on infrared wavelength light to compose and focus the image of the retina before final image capture. To achieve proper color balance on the final image recorded on the camera, many devices split off the infrared wavelengths to a second infrared sensitive image sensor to be used for focusing, and send the visible wavelength light to a separate visible light sensitive image sensor for final image capture. When a consumer camera device digital camera back is used for final image capture, this split off is required as consumer camera devices are sensitive only to visible light wavelengths.

Conventional fundus cameras require manual control of image exposure and flash power resulting in the need for multiple photos to obtain a correctly exposed image.

Many conventional fundus cameras are heavy and large and require external power and observation monitors and other systems, which add to their size and limit their mobility. True size portability and battery based power is critical for establishing mobile screening clinics where independent traveling clinicians, for example, must be able to easily set up low-cost screening programs in areas with little access to electricity and other medical equipment.

The complexity of conventional systems requires extensive training and the need for specialists to obtain adequate images of the fundus. This limits the ability to deploy fundus cameras to a large number of clinics, especially primary care clinics, and therefore prevents those who may need treatment from getting screened for retinopathy. Furthermore, many conventional fundus cameras are expensive and cannot be produced at a low cost. This also prevents deployment of the diagnostic imaging equipment necessary to screen many patients.

For non-mydriatic diagnostics, existing fundus cameras generally require the use of two separate systems for observation and photography of the fundus. In these systems an infrared imaging sensor is needed for observation and another imaging sensor is needed for visible light photography. This is particularly true when a consumer camera device body is used to record images as these devices are only sensitive to visible wavelengths of light. This has the disadvantage of adding cost, complexity in manufacture, and size to the overall fundus camera design and prevents these cameras from achieving true mobility and portability at a low cost.

CCD and CMOS sensors used in consumer camera devices are inherently sensitive to infrared wavelengths and an infrared cutoff filter is used to prevent infrared wavelengths from reaching the image sensor of the consumer camera device. If this filter were not present, significant image distortion from infrared wavelengths would be present in the recorded image. Some consumer camera devices have used a single sensor to record both infrared and visible wavelengths of light by using a mechanical filter that is automatically rotated into position and filters out infrared wavelengths when taking a normal visible spectrum photo. This is an unnecessarily complex and difficult to manufacture mechanism and this design is no longer in commercial production.

While conventional approaches discussed above may provide certain capabilities, none of their uses achieve true portability, in an inexpensive, pragmatic form so as to solve problems as described above.

SUMMARY OF INVENTION

An aspect of an embodiment of the present invention is to overcome the various problems described above, but not limited thereto, and therefore provide a new photographic device available for screening Diabetic Retinopathy and other retinal pathologies in primary care facilities and tertiary care clinics.

Effective screening strategies for tele-ophthalmology detection of DR require a low cost, low complexity, high manufacturability, high scalability, highly portable, easy to use fundus camera that can be distributed across a wide network with efficient transmission of captured images for review. In the present invention we describe a device that accomplishes each of these goals. Ease of manufacturing is achieved in part by using off the shelf components, in particular a consumer camera device that is fully integrated with the optics and illumination that enable it to take fundus photographs. In addition, ease of manufacturing is achieved by reducing the number of elements required in the complex optic and illumination path to enable fundus photography. The optical and illumination design is optimized to use off the shelf inexpensive commonly available components.

In an embodiment of the present invention, ease of use is achieved in part by taking advantage of the built-in inherent capabilities of the consumer camera device, in particular auto-focus and auto-exposure. Auto-focus is achieved by retaining the usual front lens on the consumer camera device and thru use of a combination of macro extension rings and macro optics, enhancing the normal macro capabilities of the consumer camera device to focus on the retina image formed by the front condensing lens of the fundus camera. For a DSLR type consumer camera device, manufacturing is further enhanced by incorporating the front lens into the fundus camera housing of the fundus camera itself to serve as the point of integration and attachment to the consumer camera device DSLR body. Precise modification of the focal distance of the front lens on the consumer camera device allows the consumer camera device to focus on the retina image formed by the front condensing lens over a wide range of patient refractions. In contrast, most existing fundus cameras require either manual focus by the user of the fundus camera, or complex optical mechanisms to achieve auto-focus.

An aspect of an embodiment of the present invention provides auto-exposure that may be achieved by taking advantage of built-in through-the-lens (TTL) exposure metering systems inherent in many consumer digital cameras and using a TTL enabled external flash. Conventional fundus cameras require manual control of image exposure and flash power resulting in the need for multiple photos to obtain a correctly exposed image. Whereas, regarding an aspect of an embodiment of the present invention, by incorporating the external TTL enabled flash into the fundus camera, the consumer camera device integrated into the fundus camera can correctly set image exposure. This is achieved by emission of lower power pre-flash by the external flash to determine the appropriate full flash exposure for the photograph. The timing between pre-flash and actual flash used to expose the retina is such that the pupil is unable to constrict during the interval between pre-flash and full flash. Thus, the pre-flash does not constrict the pupil such that non-mydriatic (undilated pupil) photography is possible even with a TTL based exposure system.

Many conventional fundus cameras are heavy and large and require external power and observation monitors and other systems, which add to their size and limit their mobility. True size portability and battery based power is critical for establishing mobile clinics where independent traveling clinicians, or example, must be able to easily set up low-cost screening programs in areas with little access to electricity and other medical equipment. An aspect of an embodiment of the present invention provides a battery based power that can be achieved by using low power LED lights in the fundus camera for focusing illumination and powering both the consumer camera device and external flash using their built in batteries. Portability is achieved by incorporating the consumer camera device front lens into the camera design, and simplifying the optical design, such that the additional required optical illumination and focusing elements can be contained in a housing of comparable size to a large DSLR telephoto zoom lens An aspect of an embodiment of the present invention provides the capability to improve cost and manufacturability when using a consumer camera device body for image recording. This can be achieved at least in part by modifying the consumer camera device so that its image sensor is sensitive to infrared wavelengths. This is accomplished by removal of the infrared cutoff filter that is present in each consumer camera device over the image sensor of the consumer camera device and replacing it with a clear filter of appropriate size and thickness that will pass both infrared and visible wavelengths to the image sensor. Specification of the optical properties of the clear filter are critical to retain correct exposure and auto-focus capabilities of the consumer camera device.

CCD and CMOS sensors used in consumer camera devices are inherently sensitive to infrared wavelengths and the infrared cutoff filter is used to prevent infrared wavelengths from reaching the image sensor of the consumer camera device. If this filter were not present, significant image distortion from infrared wavelengths would be present in the recorded image. Some consumer camera devices have used a single sensor to record both infrared and visible wavelengths of light by using a mechanical filter that is automatically rotated into position and filters out infrared wavelengths when taking a normal visible spectrum photo. This is an unnecessarily complex and difficult to manufacture mechanism and this design is no longer in commercial production. However, pertaining to an aspect of an embodiment of the present invention, to obtain correctly exposed color images of the retina without infrared distortion it is possible to place multiple infrared filters in front of the flash of the fundus camera so that only visible wavelengths of light produced by the flash are transmitted to the retina and reflected to the image sensor of the consumer camera device. This allows use of an infrared light source that the image sensor of the consumer camera device is sensitive to for focusing the retinal image of the eye, and then a visible light only flash to record the final color image on the image sensor of the consumer camera device. This highly manufacturable device of this embodiment requires no additional mechanical devices to perform this function, which simplifies reliability, lowers device complexity and ultimately lowers device cost. In fact, it is not even necessary to add timing circuitry to turn the infrared focusing light source off during flash photography as the light intensity produced by the flash so exceeds the light intensity of the infrared focusing light that effectively infrared wavelengths of light do not significantly contribute to the final recorded image. This again simplifies device complexity over existing non-mydriatic cameras.

An aspect of an embodiment of the present invention may be achieved by modifying an inexpensive consumer digital camera into a stand-alone mydriatic and non-mydriatic portable fundus camera which is capable of composing and acquiring images of the fundus, storing those images, and transmitting them over a wired or wireless telemedicine network to enable efficient and cost-effective retinal screening. Briefly, the transformation of a consumer digital camera to fundus camera involves several novel modifications including, but not limited to, attaching a modular optical and illumination system held in a housing to the front lens of the consumer digital camera wherein the modular system is able to produce and relay an image of the fundus to the image sensor of the camera such that the auto-focus capabilities of the camera are retained, attaching an external through-the-lens (TTL) metering enabled flash to the camera to allow for auto-exposure, and finally modification of the camera's CCD or CMOS image sensor to allow for non-dilated fundus examinations. Through the modifications, an inexpensive consumer digital camera becomes capable of producing images of the fundus comparable to existing commercial fundus cameras which cost upward of $50,000. The various embodiments of the present invention described below, for example, have a total estimated cost of perhaps under $1,000, and therefore present a significant leap forward in both the realm of manufacturability and accessibility to customers within the existing commercial fundus camera market.

It should be appreciated that rather than modifying an existing digital camera or device, the original manufacturing of the desired or required device or system and related components may be implemented as well, and shall be employed within the context of the invention.

An embodiment of the present invention portable fundus camera may include a consumer digital camera tethered to a modular attachment which provides all necessary optical and illumination components to produce an image of the fundus. The attachment interfaces with the camera in such a way that both auto-focus and auto-exposure capabilities inherent in the consumer camera are retained. By basing the design around a consumer digital camera, the present technology leverages recent advancements in consumer camera technology such as, but not limited thereto, the introduction of LiveView LCD screens, advanced TTL metering systems, image stabilization, in-camera noise reduction algorithms, etc. Cameras on the market currently suitable for the present invention include, but are not limited thereto, advanced 'prosumer' point and shoot cameras (e.g., Canon G11, Nikon P6000, Panasonic LX5) in addition to recently released micro 4/3rds cameras (e.g., Panasonic G2) which feature increased image sensor size and an interchangeable lens design. In an embodiment, the portable fundus camera may be designed for the micro 4/3rds cameras, thereby incorporating a non-changing interchangeable lens and therefore able to be easily upgraded as camera technology further develops (e.g. subsequently released cameras within the same make/model). This enables the portable fundus camera to be easily upgraded to improve image quality as digital sensor technology advances.

An aspect of an embodiment of the present invention provides for interfacing the portable fundus camera with a consumer digital camera and consequently provides the advantage of ease of operation by non-trained personnel. Operation of the novel fundus camera as described strives for a "point & shoot" approach to fundus photography. The ease of operation is an aspect of the present invention previously never achieved by fundus cameras on the market today. By retaining the built in camera shooting modes of the consumer digital camera, users of an embodiment of the present invention portable fundus camera can take a picture of a patient's retina in much the same way he or she can take the picture of an everyday object with a standard unmodified consumer camera. In brief, a user of an embodiment of the present invention camera would turn on the digital camera, turn on the illumination switch on the housing and aim the camera at a patient's eye. Image composition is achieved through the built-in LCD screen on the camera, and a properly exposed image is produced by a TTL-metered external flash when the shutter is pressed. Review of the images can be performed directly on the camera. Because operation of an embodiment of the present invention fundus camera does not differ markedly from operation of a point & shoot camera, non-trained medical personnel such as nurses or field technicians can quickly learn how to take appropriate images of the fundus without extensive and expensive training, further facilitating the feasibility of success of a wide-spread diabetic retinopathy screening program. In addition, being based on a digital camera limits an exemplary embodiment of the present invention fundus camera may have a size of approximately 5" (D)×10" (L)×5" (H). These dimensions comprise a self-powered, stand-alone fundus camera capable of acquiring, storing and transmitting images of the fundus, a feature that no other fundus camera on the market has been able to previously achieve. Size and portability are important for being able to move from exam room to exam room, and is a critical aspect for diagnosing patients with reduced mobility or infants.

Another advantage of designing an embodiment of the present invention fundus camera around a consumer digital camera is ease of manufacturing. By leveraging the low cost of mass-produced consumer cameras, desirable functions of fundus cameras such as LCD screen technology, auto-focus, auto-exposure, image stabilization, and last but not least high-resolution, low noise image sensors can be obtained at a fraction of the cost of an OEM design. This aspect of an embodiment of the present invention enables the camera to retain (and add to) many features of high-end fundus cameras at the fraction of the cost, thereby significantly reducing the price of the overall fundus camera to price points less than $1/20^{th}$ of the cost of existing tabletop fundus cameras. The cost-conscious fundus camera design of an embodiment would enable a large number of primary care practitioners both in the US and abroad to establish affordable screening programs for common retinal diseases.

The design of the modular attachment of an embodiment of the present invention, which consists of all of the optical and electrical elements necessary to produce an image of the fundus for the consumer camera to image, largely consists of low cost commercially available optical and LED circuit components. Non-limiting components comprised in the modular attachment include, but are not limited to: a front objective lens for imaging the retina of with a power approximately 22D with anti-reflection coatings, a beamsplitter, a pair of linear polarizers, a light gathering converging lens, a mirror, an annular image mask, an infrared cold mirror, a xenon flash tube and reflector assembly, heat absorbing glass, an infrared cut-off filter, a diffuser, infrared and/or visible wavelength high power LEDs and circuitry to switch on and off and power the LEDs. Non-limiting features include a shared light path between the image produced of the fundus and the illumination of the aforementioned fundus, a shared light path for both infrared and visible illumination, and the ability for the aforementioned components to be integrated with a consumer digital camera for user control, focusing, digital display, and digital storing of the image of the fundus. In an embodiment, for example, emphasis may be placed on designing the modular attachment to be small, yet ergonomic and maintain a total parts cost of less than $300.

In order for practicing ophthalmologists to diagnose retinal disease, it is necessary for them to work with high-resolution, large image field, and artifact free photographs of the fundus. These aspects are critical in identifying micro aneurysms and dot blot hemorrhages common to patients with developing diabetic retinopathy. An embodiment of the present invention portable fundus camera is capable of taking images which meet these quality requirements by taking advantage of new low-noise image sensors, as well as the macro focusing ability of the consumer digital camera. This macro ability is achieved by a novel integration and placement of the camera front lens, macro lenses, and the front objective lens, thereby allowing the fundus image to fill the image sensor and thus capture details ordinarily lost under standard non-macro imaging. An artifact and reflection free image of the retina is produced by a method of illumination present in many existing commercial fundus cameras in which an annular ring of light is focused on the cornea by means of a front objective lens. As this focused ring of light travels through anatomical elements of the eye (cornea, anterior cavity, lens and posterior cavity), it expands to fill the retina. The fully illuminated image retina is then relayed through the front objective lens to produce a retinal field of approximately 50°, which is subsequently relayed to the consumer camera's front lens and finally to the image sensor of the camera. In addition to using the aforementioned annular illumination technique, an embodiment of the present invention portable fundus camera introduces a novel application of cross-polarization using a pair of low-cost linear film polarizers in order to further reduce corneal haze and reflection artifacts from the front lens.

The success of a wide-spread retinal disease (e.g. Diabetic Retinopathy) screening program is largely dependent upon the speed and efficiency of photography patient's eyes. Typically, patient's eyes have to be dilated in order to maintain a sufficiently large pupil diameter to allow for fundus photography. Commercial dilating drops often take upward of 30 minutes to take effect and significantly increase the time required to move patients in and out of the clinic. Therefore, an embodiment of the portable fundus camera should be capable of non-mydriatic imaging, or in other words, do not require the patient to be dilated. Previously, this has been accomplished by installing a separate infrared sensitive CCD or CMOS sensor and illuminating the patient with infrared light. Because the human eye is not sensitive to infrared wavelengths, the patient's pupil can maintain a sufficiently large diameter in a low-lit room to allow for unobstructed fundus photography. An aspect of an embodiment of the present invention follows a similar technique for enabling non-mydriatic imaging, but incorporates a novel aspect in that a single sensor is used for both infrared imaging and visible light imaging for capturing the final fundus image. In brief, this aspect of the design involves removal of the infrared filter placed in front of all consumer digital cameras and filtering the infrared light from the incoming final image acquisition illumination source, thereby allowing non-mydriatic infrared image composition while maintaining a properly exposed and color-balanced final image of the fundus.

Associated with the aforementioned aspects, another aspect of an embodiment is to serve as a basis for a telemedicine-based screening program. This program may include a secure online database which will be automatically managed. Clinicians will be able to upload the images taken from our camera into this database. On the receiving end of this system will be a team of specialists who can then virtually examine each patient and determine if there are signs of Diabetic Retinopathy or other retinal diseases. This method and related system will enable high throughput of patient diagnostic information and will be a major improvement over the current practice of referring patients to specialists. Patients at risk for Diabetic Retinopathy will be able to be screened at the convenience of their own primary care clinic. Being less reliant on expensive retinal imaging equipment, the new screening methods will also be able to be deployed in developing countries where there are currently limited diagnosing centers or certified physicians. As such, the proposed portable fundus camera has the potential to save the vision of millions of at-risk patients.

An aspect of an embodiment of the present invention, a hand-held portable fundus camera, as embodied and broadly described herein, comprises a module optical system which is capable of being integrated with a portable independent image recording device for photographing the fundus of an eye, the independent image recording device comprises a recording device observation optical system and a recording device photography system, the recording device observation optical system and the recording device photography optical system sharing a common optical path, and the module optical system comprising a housing, a module optical path which is common to the recording device observation optical system and recording device photography system when the independent image recording device is integrated with the module optical system, a front objective lens, a module illumination optical system where an illumination optical path of the module illumination optical system is partially shared with the module imaging optical path and the illumination optical path is coaxial with the module imaging optical path by a beam splitter wherein the module illumination optical path is reflected of the beam splitter whereby the illumination optical path is directed through the front objective lens, and coupling means for coupling the module optical system with the independent image recording device.

In another aspect of an embodiment of the present invention, the module illumination optical system further comprises an observation lights source, a photographing light source, and a hot mirror filter wherein the observation light source and the photographing light source share the illumination optical path through the means of the hot mirror filter which is disposed coaxial to the illumination optical path, the hot mirror filter blocking infrared light being emitted from the photographing light source and redirecting light from the observation light source into the illumination optical path.

In another aspect of an embodiment of the present invention, a hand-held portable fundus camera comprises an illumination optical system for illuminating the fundus of an eye, an observation optical system for observing the fundus, and a photography optical system for photographing an image of the fundus, the camera comprising a front objective lens, an observation light source, a photographing light source, a beam splitter, and a CCD imaging element wherein the observation optical system and the photography optical system share a common optical path, wherein the observation optical system and photography optical system share the CCD imaging element, wherein the common optical path is further partially shared by a illumination optical path of the illumination optical system wherein the beam splitter is disposed in the common optical path coaxial to the illumination optical path whereby the illumination optical path is reflected off the beam splitter and directed through the front objective lens, and wherein the illumination optical system delivers only infrared light to the CCD imaging element when observing the fundus by the observation optical system and delivers only visible light to the CCD imaging element when photographing the fundus through the photography optical system.

In another aspect of an embodiment of the present invention, a hand-held portable fundus camera comprises an illumination optical system for illuminating the fundus of an eye, an observation optical system for observing the fundus, and a photography optical system for photographing an image of the fundus, and the camera further comprising a front objective lens, and a beam splitter, wherein the observation optical system and photography optical system share a common optical path, and wherein the common optical path is further partially shared by a illumination optical path of the illumination optical system through the means of the beam splitter whereby the illumination optical path is reflected off the beam splitter and directed through the front objective lens.

An aspect of an embodiment of the present invention provides a hand-held portable fundus camera system and related method of use and manufacture. The hand held fundus camera system (and related method of use and manufacture) may comprise: a module optical system capable of being integrated with a consumer camera device for auto focus photography by the consumer camera device of the fundus of an eye. The module optical system may comprise: a composing image acquisition illumination observation source (e.g., photographing light source); a final image acquisition illumination source (e.g. observation light source); an optical separator and transmitting means (e.g., IR filter, heat absorbing glass, cold mirror/beam splitter or the like) for separating and transmitting the composing image acquisition observation illumination source and the final image acquisition illumination source to an image mask, of which is relayed to the retina of the fundus through the use of a redirecting mirror, a beam splitter and a front objective lens. The image mask may be configured to provide light that illuminates the retina to output an image that is relayed through the objective lens and captured by the consumer camera to provide an image of the retina. Also included is a module interface system (e.g. macro lenses, physical couplings, macro extension ring) to integrate the module optical system with the consumer camera device. It should be appreciated that the module interface system enhances the macro focusing capability of the consumer camera device to enable auto-focus photography by the consumer camera device of the fundus image produced by the front objective lens.

An aspect of an embodiment of the present invention provides a hand-held portable fundus camera system and related method of use and manufacture. The hand-held portable fundus camera system (and related method of use and manufacture) may comprise a module optical system capable of being integrated with a consumer camera device for photographing the fundus of an eye. The module optical system may comprise: a composing image acquisition illumination observation source (e.g., photographing light source); a final image acquisition illumination source (e.g. observation light source); and an optical separator and transmitting means (e.g., IR filter, heat absorbing glass, cold mirror/beam splitter) for separating and transmitting the composing image acquisition observation illumination source and the final image acquisition illumination source to an image mask the image mask, of which is relayed to the retina of the fundus through the use of a redirecting mirror, a beam splitter and a front converging lens. The module optical system may further comprise: the image mask being configured to provide light that illuminates the retina to output an image that is relayed through the front objective lens and captured by the consumer camera device to provide an image of the retina. The consumer camera device may comprise a consumer point and shoot or digital single lens reflex system (DSLR) module for automated image capture and review. The consumer camera device may further comprise: an external flash device; a hot shoe adapter in communication with the external flash device, wherein the captured image being provided by the consumer camera device being in communication with the final image acquisition illumination source. Moreover, the captured image may be properly exposed by the consumer camera device being in communication with the final image acquisition illumination source, wherein the external flash device comprises through the lens (TTL) metering to allow the consumer camera device to provide properly exposed images of the retina.

An aspect of an embodiment of the present invention provides a hand-held portable fundus camera system and related method of use and manufacture. The hand-held portable fundus camera system (and related method of use and manufacture) may comprise a module optical system capable of being integrated with a consumer camera device for photographing the fundus of an eye using infrared illumination for focusing of the image by the consumer camera device. The module optical system may comprise: a composing image acquisition illumination observation source (e.g., old: photographing light source), wherein the wavelength of the image acquisition illumination source is infrared; a final image acquisition illumination source (e.g., xenon flash tube); and an optical separator and transmitting means (e.g., IR filter, heat absorbing glass, cold mirror/beam splitter) for separating and transmitting the composing image acquisition illumination observation source and the final image acquisition illumination source to an image mask, of which is relayed to the retina of the fundus through the use of a redirecting mirror, a beam splitter and a front objective lens. The module optical system may further comprise the image mask configured to provide light that illuminates the retina to output an image that is relayed through the front objective lens and captured by the consumer camera to provide an image of the retina. The optical separator and transmitting means may further comprise at least one or more of 'a', 'b', or 'c'. Whereby 'a', 'b', or 'c' may include the following: a) separating and transmitting the composing image acquisition illumination observation source that is of infrared wavelengths and the final image acquisition illumination source that is of visible wavelengths; b) separating and transmitting the composing image acquisition illumination observation source that is of visible and infrared wavelengths and the final image acquisition observation illumination source that is of visible and infrared wavelengths; c) separating and transmitting the composing image acquisition illumination observation source that is of visible wavelengths and the final image acquisition illumination source that is of infrared wavelengths. The fundus camera may further comprises of at least one of: an infrared cutoff filter optically disposed between the final image acquisition illumination source and the optical separator and transmitting means; or an infrared cutoff filter optically disposed between the composing image acquisition illumination source and the optical separator and transmitting means. And wherein the consumer camera device may comprise a consumer point and shoot or digital single lens reflex system module for automated image capture and review, whereby an infrared filter has been removed or bypassed from the consumer point and shoot or the digital single lens reflex system module and replaced with a full spectrum filter. The consumer camera device may further comprises: an external flash device; a hot shoe adapter in communication with the external flash device, whereby the captured image being provided by the consumer camera device being in communication with the final image acquisition illumination source; and wherein the captured image being properly exposed by the consumer camera device being in communication with the final image acquisition illumination source; and wherein the external flash device comprises through the lens (TTL) metering to allow the consumer camera device to provide properly exposed images of the retina.

An aspect of an embodiment of the present invention relates to the modification and integration of an existing consumer digital camera, for example, with an optical imaging module to enable point and shoot fundus photography of the eye. The auto-focus macro capability of existing consumer cameras is adapted to photograph the retina over an extended diopter range, eliminating the need for manual diopter focus adjustment. The thru-the-lens (TTL) auto-exposure flash capability of existing consumer cameras is adapted to photograph the retina with automatic flash exposure eliminating the need for manual flash adjustment. The consumer camera imaging sensor and flash are modified to allow the camera sensor to perform both non-mydriatic focusing of the retina using infrared illumination and standard color flash photography of the retina without the need for additional imaging sensors or mechanical filters. These modifications and integration of existing consumer cameras for fundus photography of the eye significantly improve ease of manufacture and usability over existing fundus cameras.

An aspect of an embodiment of the present invention provides hand-held portable fundus camera system comprising a module optical system capable of being integrated with a consumer camera device for photographing the fundus of an eye of a subject using infrared illumination for focusing of the image by the consumer camera device.

Available methods for the fabrication of any and all of the embodiment, systems, devices, compositions, materials, computer program logic, computer processing, and components discussed throughout this disclosure are also considered part of the present invention. A method of manufacturing of any and all of the embodiments, systems, devices, compositions, materials, computer program logic, computer processing, and components discussed throughout this disclosure may be employed within the context of the invention.

Additional aspects and advantages of various embodiments of the invention will be set forth in part in the description which follows and in part will be obvious from the description, or may be learned by practice of various embodiments of the invention. The aspects and advantages of various embodiments of the invention may be realized or attained by means of the instrumentalities and combinations particularly pointed out in the appended claims.

Aspects of various embodiments of the invention itself, together with further objects and attendant advantages, will best be understood by reference to the following detailed description taken in conjunction with the accompanying drawings.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of aspects of various embodiments the invention. The drawings are provided only for the purpose of illustrating select embodiments of the invention and are not to be construed as limiting the invention.

FIG. 11 illustrates the effect of the digital subtraction of spectral content of back light reflections practicing an embodiment of the present invention.

FIG. 12 illustrates the effect of the digital subtraction of back light reflections by combining multiple images practicing an embodiment of the present invention. Retinal image no. 1 (FIG. 12A) is combined with retinal image no. 2 (FIG. 12B) to provide a combined image (FIG. 12C) without back light reflections.

FIG. 13 illustrates the effect of digital enhancement of central white balance practicing an embodiment of the present invention.

FIG. 14 illustrates practicing an embodiment of the present invention.

FIG. 15A, FIG. 15B, and FIG. 15C illustrate practicing an embodiment of the present invention. FIG. 15A and FIG. 15B illustrate an embodiment using a Panasonic Lumix G2 consumer camera device. FIG. 15C illustrates the resultant fundus image practicing a mydriatic embodiment.

DETAILED DESCRIPTION OF THE INVENTION

Figure 1A:
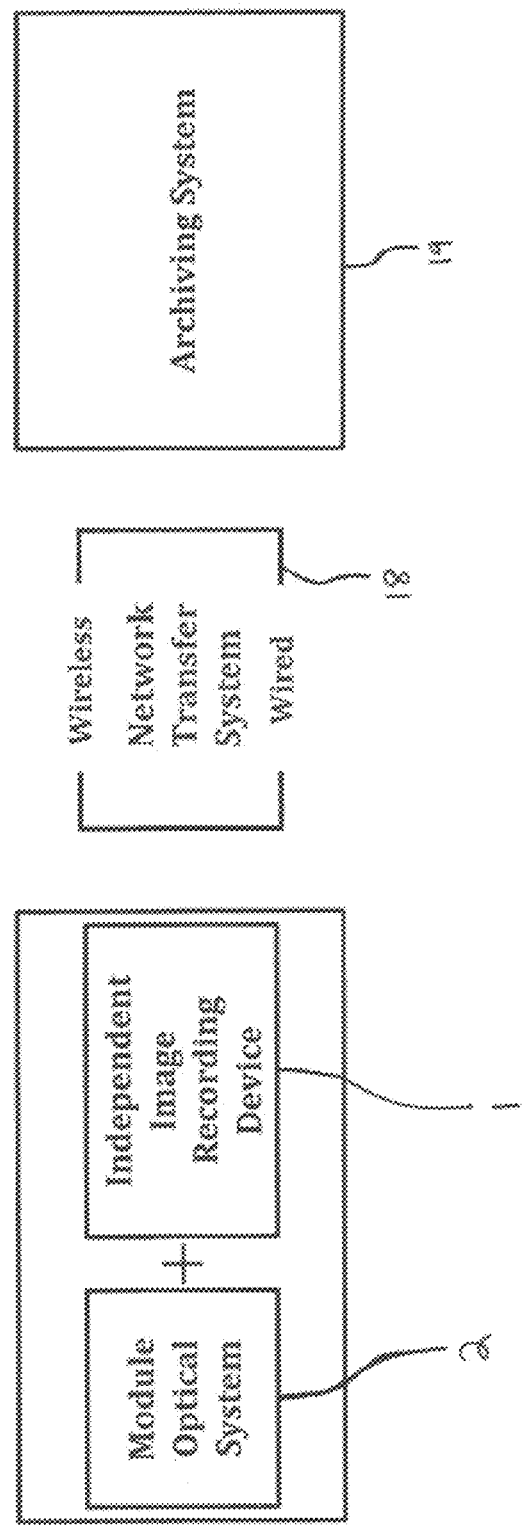
FIG. 1A provides a schematic block diagram of an embodiment of the system for capturing and storing images of the fundus.

An embodiment of the present invention is provided below with reference to the accompanying drawings. FIG. 1A provides a block diagram of the embodiment of the present invention which indicates the basic component parts of the system for photographing the fundus and storing images. The fundus camera may consist of a module optical system 2 which provides the optical and illumination means necessary to produce and image the retina. This module optical system 2 may be attached to an independent image recording device 1, which provides the means of previewing the fundus photographs, photographing the fundus, and storing images. In an embodiment, but not limited thereto, the independent image recording device 1 consists of a consumer digital camera or device. The integration of the module optical system 2 and the independent image recording device 1 mydriatic and non-mydriatic portable fundus camera which is capable of composing and acquiring images of the fundus, storing those images, and transmitting them over a wired or wireless telemedicine network to enable efficient and cost-effective retinal screening. In an embodiment, these photographs are stored on the independent image recording device until they can be transferred via a network transfer system 18 to an archiving system 19 for later diagnostics. The network transfer system 18 may transfer the photographs on the independent image recording device 1 either through wired data transfer means or via wireless data transfer means.

Figure 1B:
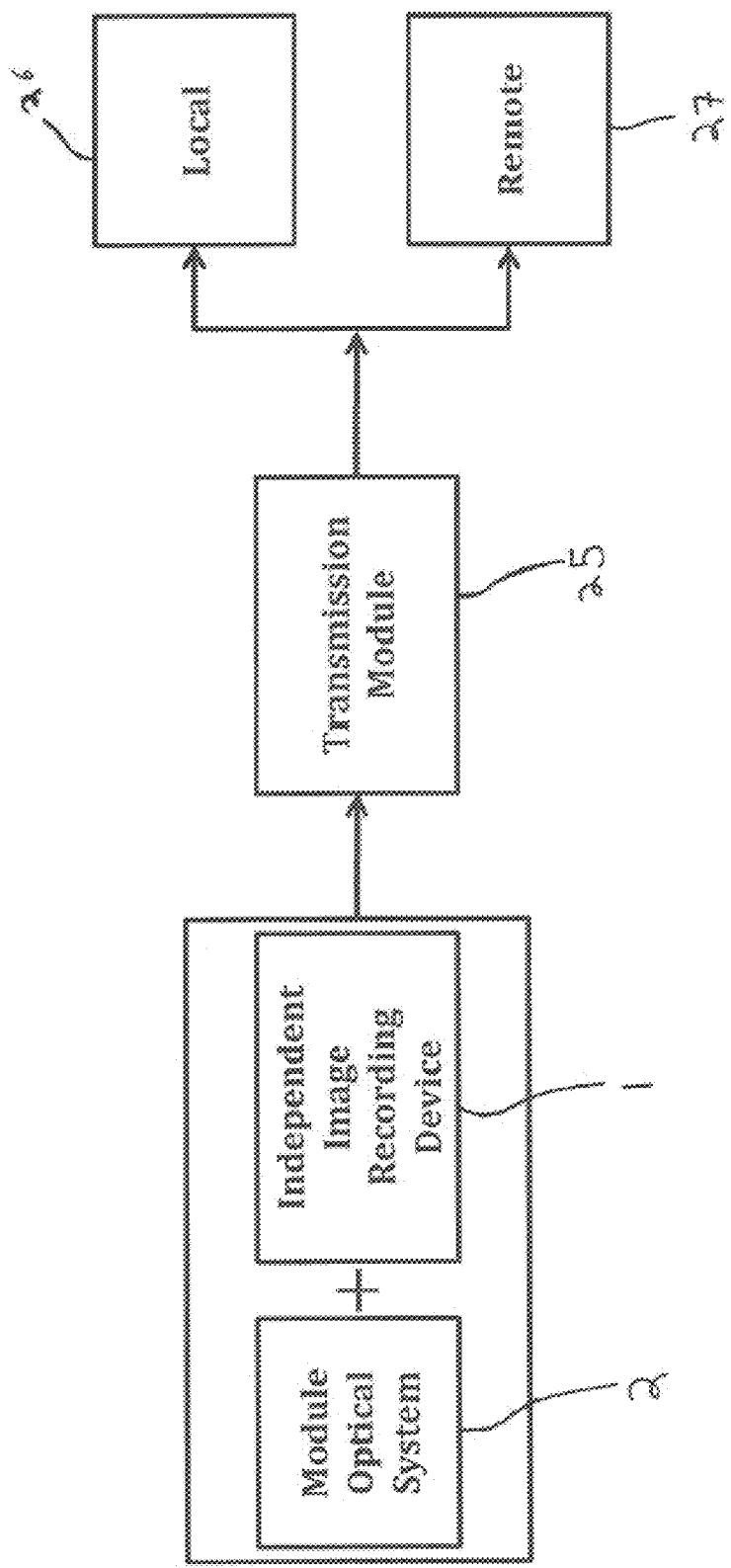
FIG. 1B provides a schematic block diagram of an embodiment of the system for capturing images and including communication between the system and local and remote locations.

FIG. 1B provides a block diagram of how images stored on the independent image recording device 1 may be communicated through a transmission module 25 to either a local 26 and/or remote 27 location. It should be appreciated that the local and/or remote location may include, but are not limited thereto, a user, a processor, a display, a database, an archive, or any combination thereof. This may enable specialists to complete diagnostics using the images at local or remote locations and enable telemedicine practices to be used. In using telemedicine practices, the images may be transmitted through the transmission module 25 to a remote location 27 where they are later reviewed by ophthalmologists or other trained specialists. If the image shows that the patient has a disease or defect, the patient may then be referred to a specialist for more testing and treatment. In this situation, images of the fundus can be recorded at a primary care clinic without the need for specialists at the primary care clinic to perform the diagnosis. Reviewing images by specialists at a remote location may allow for more efficient processing and diagnostics of the recorded images. This may allow a greater number of patients to be screened for retinal diseases at a lower overall cost.

Figure 8:
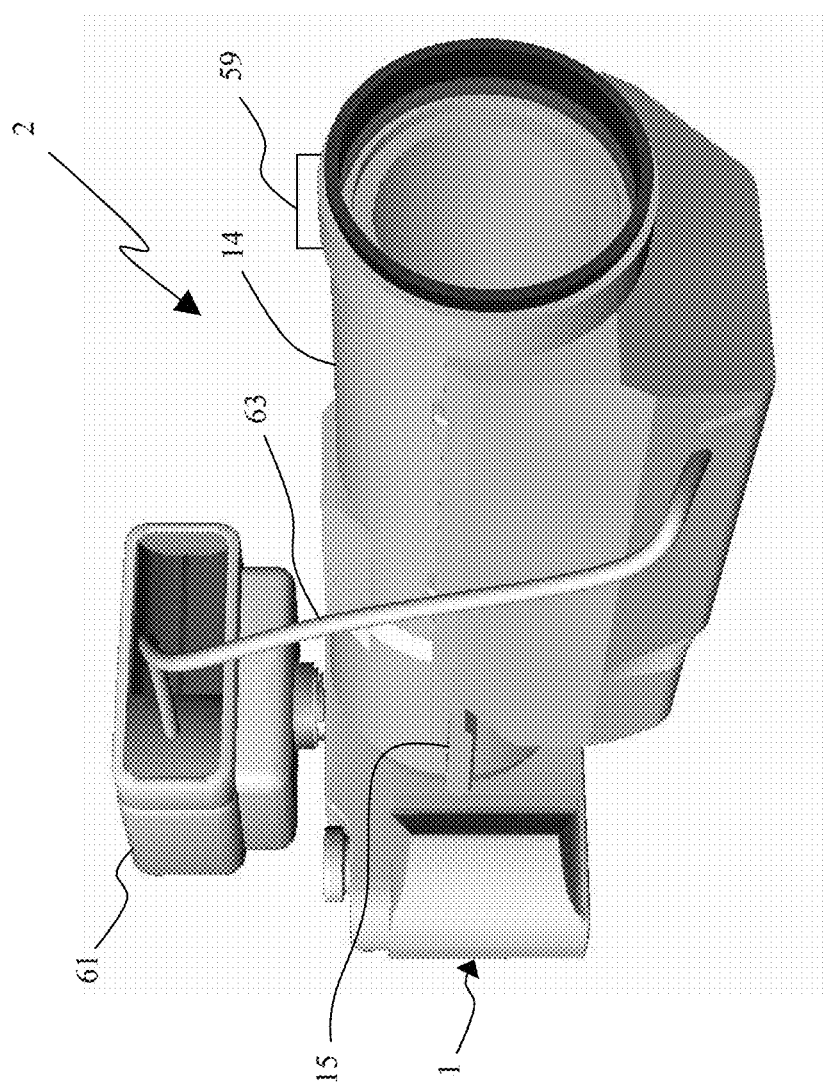
FIG. 8 provides an external schematic view of an embodiment of the portable fundus camera FIG. 9 provides a schematic illustration of an annular ring of light used to illuminate the retina FIG. 10 schematically illustrates a means of polarization to eliminate lens back reflections and corneal haze.

FIG. 8 depicts the exterior design of an embodiment of portable fundus camera. It should be noted that the module optical system 2 and peripheral components 61 are placed in such a way that they are in direct communication with the consumer digital camera 1. In an embodiment, the consumer digital camera is one of the 'point & shoot' variety aimed primarily at advanced 'prosumer' camera users in the current personal digital camera market. These cameras include, but are not limited to, the following features: a low-noise image sensor of the CCD or CMOS variety 53, a hot-shoe adapter 3 to interface with an external flash 61, an LCD screen for LiveView 51, a front lens 35 which can either be detachable or integrated to the consumer digital camera, the ability to perform auto-focus and macro-focus, the ability to auto-expose images through the use of through-the-lens (TTL) metering systems, and the availability of user-set custom modes to assist users of the portable fundus camera to easily obtain high-resolution, properly exposed and properly focused images of the fundus. In the present embodiment, the consumer camera are of the variety easily operated by untrained personnel and may be, but not limited to, advanced point & shoot cameras such as the Canon G11 and Nikon P6000, or newer mirrorless camera systems (Micro 4/3rds) such as the Panasonic G2 or Samsung NEX-1.

FIGS. 2A, 2B, 2C and 5A illustrates an aspect of an embodiment of the optics and illumination components involved in the module optical system 2 which is capable of being integrated with the consumer digital camera 1 to transform the consumer camera into a portable fundus camera. An embodiment of the module optical system 2 may include two central optical paths: an imaging optical path and an illumination optical path. The following components may be disposed along these optical paths: a front objective lens 4, a beam splitter 7 which may be disposed along the module imaging optical path and is coaxial with the front objective lens 4, a light trap 6 located above the beam splitter 7, a mirror 8, a converging lens 9, an image mask 10, a diffuser 10, two linear polarizers 41 and 43, a cold mirror or beamsplitter 11, heat absorbing glass 31, infrared cut-off 67, a composing image acquisition illumination observation source 13, a final image acquisition illumination source 12, a housing 14, and finally a coupling system 15 for attaching the module optical system 2 to the independent image recording device 1. The module optical system 2 will be described by describing the operation of an observation and photography optical system generally disposed along the module imaging optical path and by describing an illumination optical system generally disposed along the illumination optical path.

Figure 5:
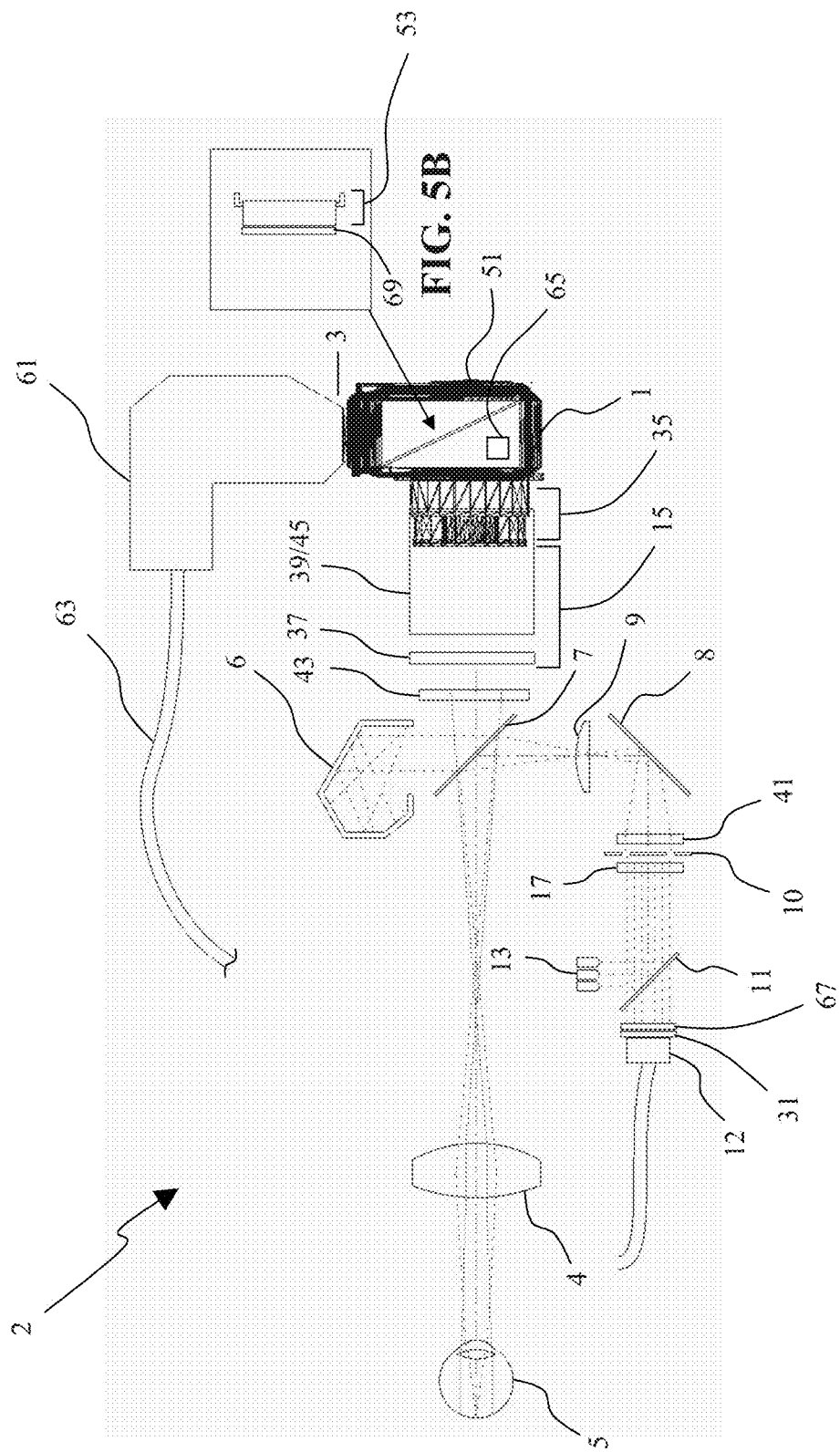
FIG. 5A provides a schematic view of various components for mydriatic or non-mydriatic imaging of the portable fundus camera as described.
FIG. 5B provides an exploded view of a depiction of the imaging sensor of the consumer digital camera and related of the portable fundus camera as described.

Referring to FIG. 5A, the illumination optical path 24 (not specifically referenced in FIG. 5A) includes the retina 5, front objective lens 4, beam splitter 7, second polarizer 43, and macro lens 37. Still referring to FIG. 5A, the module imaging acquisition optical path 23 (not specifically referenced in FIG. 5A) includes the retina 5, front objective lens 4, beam splitter 7, light trap 6, rear converging lens 9, redirecting mirror 8, first polarizer 41, image mask 10, diffuser 17, hot mirror filter 11, composing image acquisition illumination observation source 13, IR filter 67, heat absorbing glass 31, and final image acquisition illumination source 12.

Optical Path of Illumination

Figure 9:
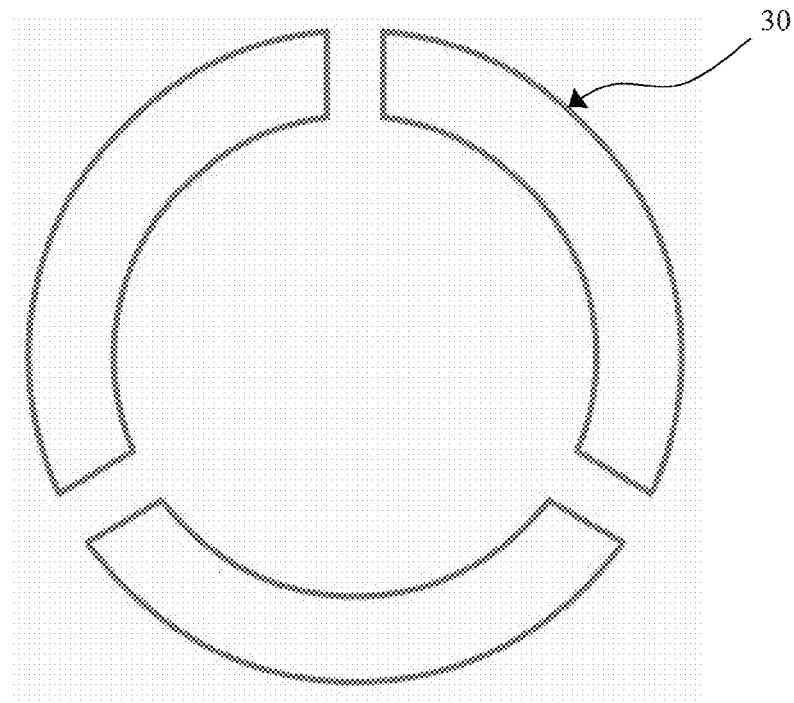

In order to view and photograph the retina, effective illumination of the back (fundus) of the eye 5 would generally be required. This may be accomplished by focusing a bundled donut of light with an outer diameter of roughly the size of a person's pupil, with an inner diameter slightly smaller than the outer, as depicted as the annular ring 30 in FIG. 9. An embodiment of the present invention has taken this illumination approach because it provides uniform lighting while minimizing corneal reflections.

In an embodiment of the invention, the illumination optical path is at first directed parallel to the module imaging optical path. Illumination light is provided by a composing image acquisition illumination observation source 13 and a final image acquisition illumination source 12. The illumination light for observing, previewing, and composing the image may be provided by the composing light source 13. The composing light source 13 may be provided by either visible-light LEDs in the mydriatic case (dilated), or infrared LEDs in the non-mydriatic case (non-dilated). By using new LED technology, embodiments of the invention are able to provide high-intensity visible or infrared lighting while requiring very little power and very little space. To provide even higher intensity light necessary to image the fundus under conditions of cross-polarization (later described below) a series of multiple LEDs, perhaps three, may be arranged in a circular pattern to provide brighter, more uniform illumination. In order to decrease the risk of ocular hazard to the eye, visible LEDs should be of the warm white type, with perhaps a color temperature of about 2700K in order to decrease exposure of the retina to wavelengths below about 450 nm. These wavelengths, which are closest to the UV range, are extremely hazardous to retinal cells when exposed for extended periods of time. Further, for non-mydriatic imaging, the LED may have a wavelength between about 700 nm and about 1200 nm. In an embodiment, the infrared LED has a wavelength of about 750 nm to reduce minor differences in focal range between the composing light source 13 and final image acquisition light source 12. The final image acquisition illumination source 13 is used for providing adequate light for photography and may be provided by a xenon flash bulb. This xenon flash tube is further connected upstream to an external TTL-enabled flash 61, which is further connected to a hot shoe adapter 3 on the consumer camera 1. In an embodiment, both the composing image acquisition illumination observation source 13 and final image acquisition illumination source 12 are oriented so that their light paths are perpendicular to each other and centered on a cold mirror or beamsplitter 11 which is angled at forty-five degrees and exists coaxial with the overall illumination optical path. The cold mirror or beamsplitter 11 redirects the composing image acquisition illumination observation source 12. More specifically, a cold mirror is used in the non-mydriatic case to redirect only the visible (about 400 nm-700 nm) wavelengths to the eye during final image acquisition, whereas an ordinary beamsplitter is used in the mydriatic case. Further, in the non-mydriatic embodiment, heat absorbing glass 31 and an infrared cut-off filter 67 is placed in front of the xenon flash tube to further block infrared light from the final image acquisition illumination. The cold mirror or beamsplitter 11, infrared cut-off filter 67, and heat absorbing glass 31 all act in concert to form an optical separator and transmitting means to provide the necessary composing illumination 13 and final image acquisition illumination 12 in order to form a final image of the fundus which is free from infrared light contamination. In an embodiment, it is important to note that this separation is achieved without the use of a mechanical mechanism.

After either passing through or being redirected by the cold mirror or beamsplitter 11, the light from either composing image acquisition illumination observation source 13 or the final image acquisition illumination source 12 may now pass through a diffuser 17 which increases uniformity of the light. Next, the light passes through an image mask 10 which has a donut cut-out. This will create the bundled donut of light needed for effective illumination of the eye 5 as described above. The masked image of light may then pass through the first of a pair of polarizers 41 in order to create plane-polarized light in at a specific angle. In an embodiment, the polarizer is of the inexpensive linear film type. The masked donut of light is then redirected by a mirror 8 angled at about 45°, and then projected through a small inexpensive converging lens 9. The redirecting mirror 8 is oriented perpendicular to the module imaging optical path. The light may then be directed toward the eye by being reflected off the beam splitter 7. The beam splitter 7 may be about a 50/50 or about 30/70 transmission and reflectance beam splitter which is coaxial with the module imaging optical path. Using a beamsplitter with a greater reflectance-to-transmission ratio results in much less ocular hazard to the patient's eye, and is therefore an important aspect of an embodiment to be considered. It should also be appreciated that embodiments may use dichroics, such as a triple dichroics in place of the beam splitter to achieve predictable results. Upon being reflected by the beam splitter 7, the light along the illumination optical path splits into two separate light paths, each with decreased intensities of the original corresponding to the specific type of beamsplitter used.

To prevent back reflections off of the light path not illuminating the eye, there may exist a light trap 6 disposed above the beam splitter 7 along one of the branches of the illumination optical path which is lined with black absorbing felt or an absorbing neutral density filter to effectively capture and trap the light from causing adverse artifacts on the final image. The light trap 6 may have walls that are built in such a way that the majority of light passing through the beam splitter 7 is reflected internally within the light trap 6. The light trap 6 is also disposed at a predetermined distance above the beam splitter 7 so as to reduce the intensity of the light falling on the light absorbing material. The existence of the light trap 6 eliminates the inherent back reflections caused by using a beam splitter 7 on the final image of the retina, and thus improves image quality drastically.

The main branch of the illumination optical path split by the beam splitter 7, now with only about 30-50% of the original intensity, may now be directed toward the front objective lens 4 along the module optical imaging path towards the eye 5. In an embodiment, the front objective lens 4 may be a standard lens normally used for indirect opthalmoscopy, which is widely available. The front objective lens 4 may normally be about 50 to 60 mm in diameter and thus provides a large image field of about 50 degrees adequate for diagnosing diseases of the vasculature of eye. In addition, these lenses most commonly have working distances of close to 50 mm as well, which provides a safe and reasonable distance from the front of the device and the patient's eye 5. This feature may be provided to enhance patient comfort during the screening process as the camera never comes close to being able to physically contact the patient's eye.

It should be appreciated that at this point, the module imaging optical path and illumination optical paths are common and the illumination optical path travels through the front objective lens 4. Introducing the beam splitter 7 at this point allows the working distance (distance between the front objective lens and the eye) of the camera to be increased and results in easier and more convenient operation. This is easier on the patient and requires less accurate positioning of the camera in order to acquire adequate images of the fundus. Thus, those taking the photographs will require less training and need less time for adequate imaging of the fundus. It should be also be appreciated that embodiments may use dichroics, such as a triple dichroics in place of the beam splitter to achieve predictable results The introduction of the beam splitter 7 at this point also results in a back reflection on the front objective lens 4. The size and intensity of this back reflection is largely a function of the distance between the image mask 10 and front objective lens 4. Thus, this distance must be optimized to reduce this reflection as much as possible while still illuminating the eye effectively. Commercially available indirect ophthalmoscopy lenses normally have advanced antireflection coatings as well which work further to reduce the central reflection. In an embodiment, the front objective lens 4, may be the OI-222 lens made by Ocular Instruments. This lens expands the image of the retina, makes it optically flat, and also has advanced antireflection coatings. In an embodiment, using a commercially available lens such also further simplifies the manufacturing process by eliminating the need to design and manufacture a unique objective lens. Methods of eliminating this back reflection present in an embodiment are through the use of a pair of polarizers 41/43 displaced perpendicularly to each other, or through image processing algorithms (for example an image processing module or component 25, both of which are described in detail below.

Once the light has passed through the front objective lens 4, the bundled donut of light is now focused at a fixed distance from the front objective lens 4 which also is the location of the front of the eye (cornea). In an embodiment, this distance is roughly 55 mm. Once light is focused on the front of the eye, it is then passed through the cornea, through the aqueous humor, through the lens of the eye, and finally through the vitreous humor to reach the retinal surface. In this process, the donut of light disperses and provides a uniform circle of light without a hole in the middle, thus illuminating the entirety of the retinal surface. During this process, the pupil of the eye is not constricting because the eye is not sensitive to infrared wavelengths in the non-mydriatic case, or in the mydriatic case the pupil is dilated and not allowed to constrict.

Imaging Optical System

Figure 2A:
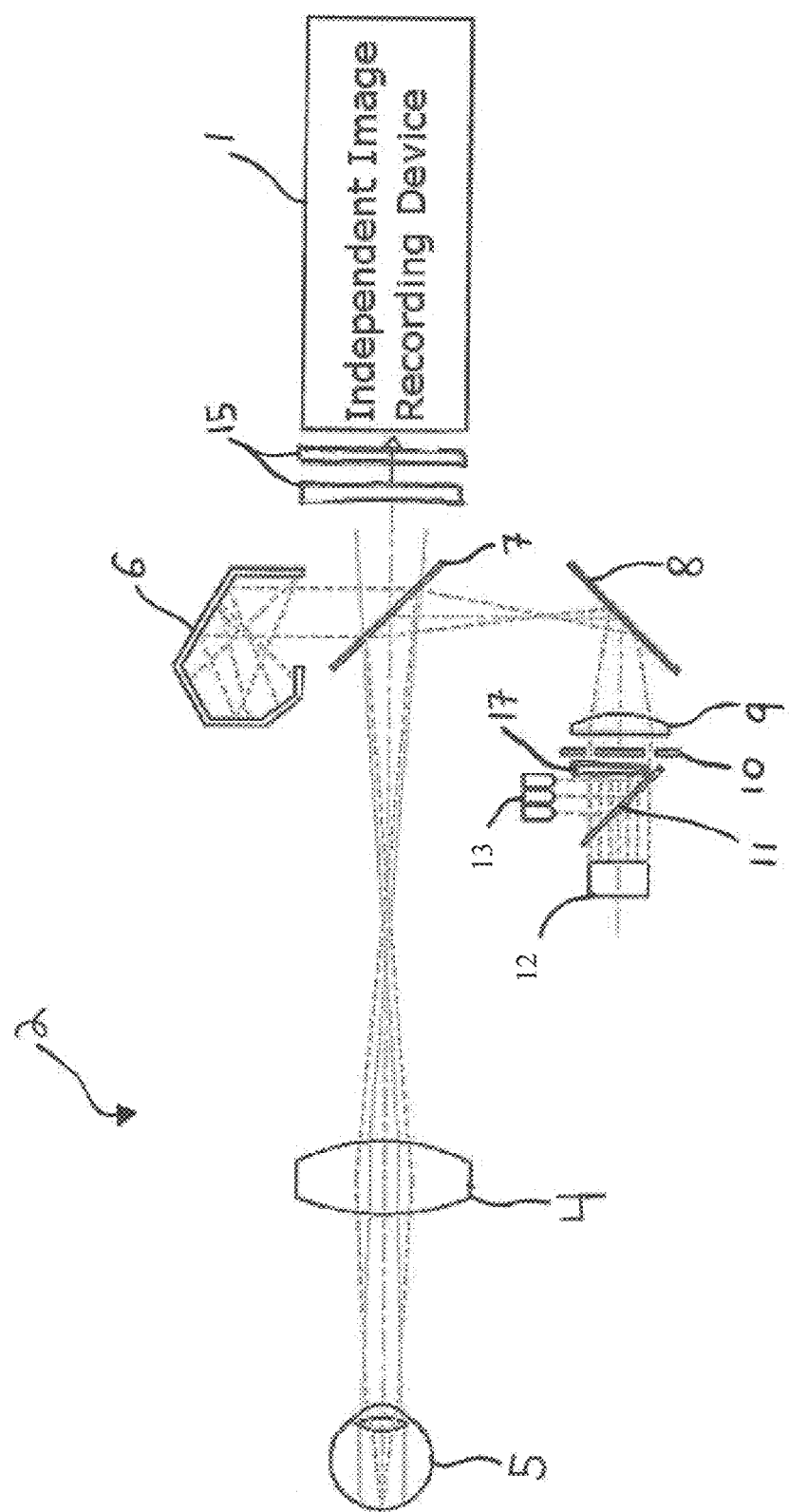
FIG. 2A provides a schematic view showing a structure of a module optical system to be connected with an independent image recording device of an embodiment.
Figure 2B:
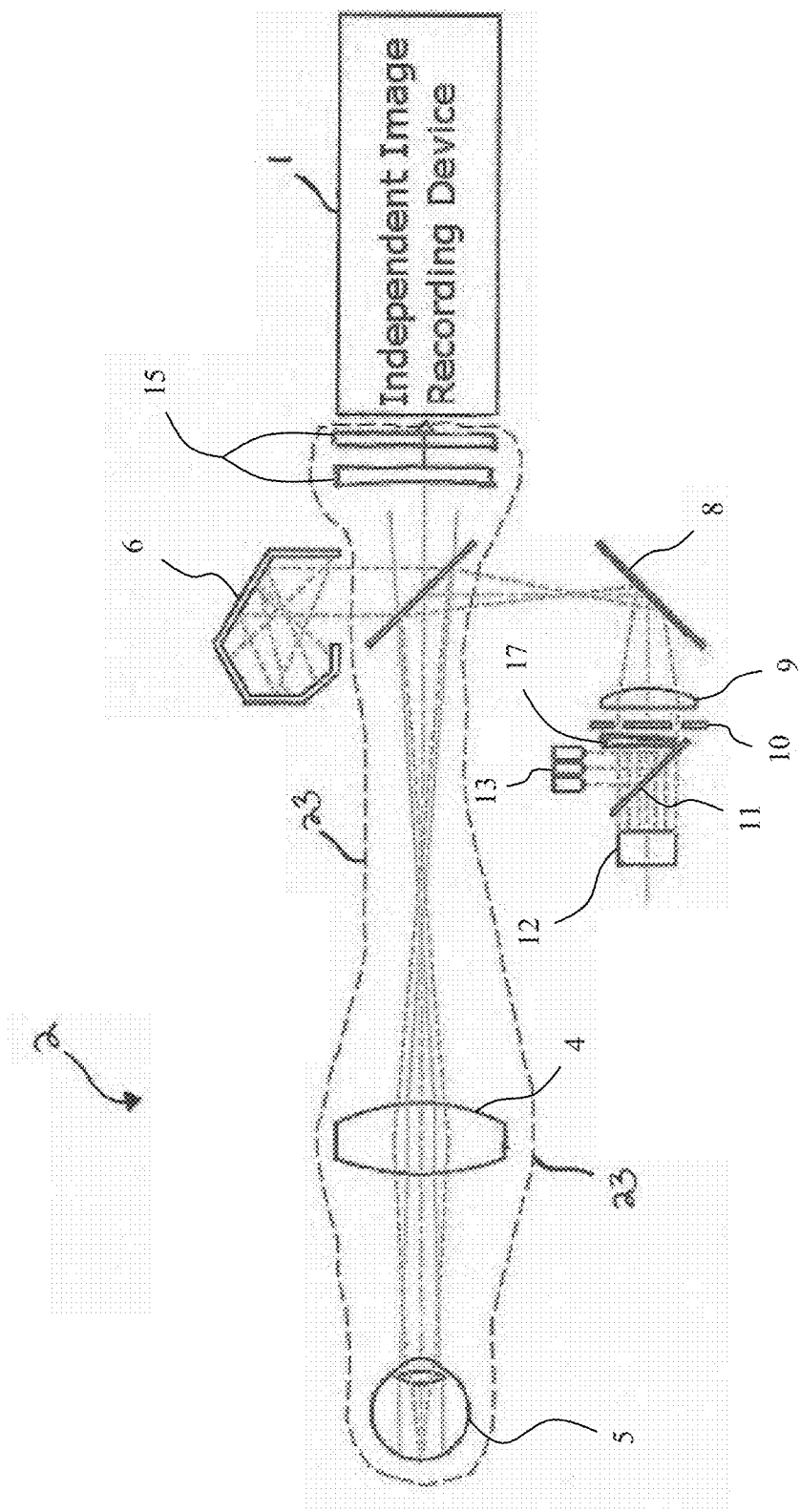
FIG. 2B provides a schematic view of the module imaging optical path of an embodiment.

Once illuminated, the image of the retina is then reflected and passes back through the front objective lens 4, through the beam splitter 7 (and also loses another 30-50% of light), and through the second polarizer 43, through a set of macro lenses 37 which expand the image, and finally through the front lens 35 to be projected onto the image sensor 53 of the consumer digital camera 1. In the non-mydriatic case, it is important to note that the infrared cut-off filter 69 inherently installed on all consumer digital cameras is removed. This enables the consumer camera to be sensitive to infrared light and is a necessary modification to allow non0mydriatic imaging. In addition, it should be appreciated that the macro lenses 37 may either be included in the module optical system 2 or incorporated with the front lens of the consumer camera 1. In FIG. 2B, the module imaging optical path 23 is shown. As the figure shows, the module imaging optical path is shared by both the observation optical system and the photographing optical system when integrated with the independent image recording device 1. Therefore, in an embodiment, the optical path is common between the observation optical system and the photographing optical system and requires only the photoelectric imaging elements of the independent recording device 1 for both observation and photography of the fundus. Embodiments of the invention, as described previously through the use of a discrete optical separator and transmitting means, eliminates the need for infrared photoelectric imaging elements for observation and visible-light photoelectric imaging elements for photography.

Figure 2C:
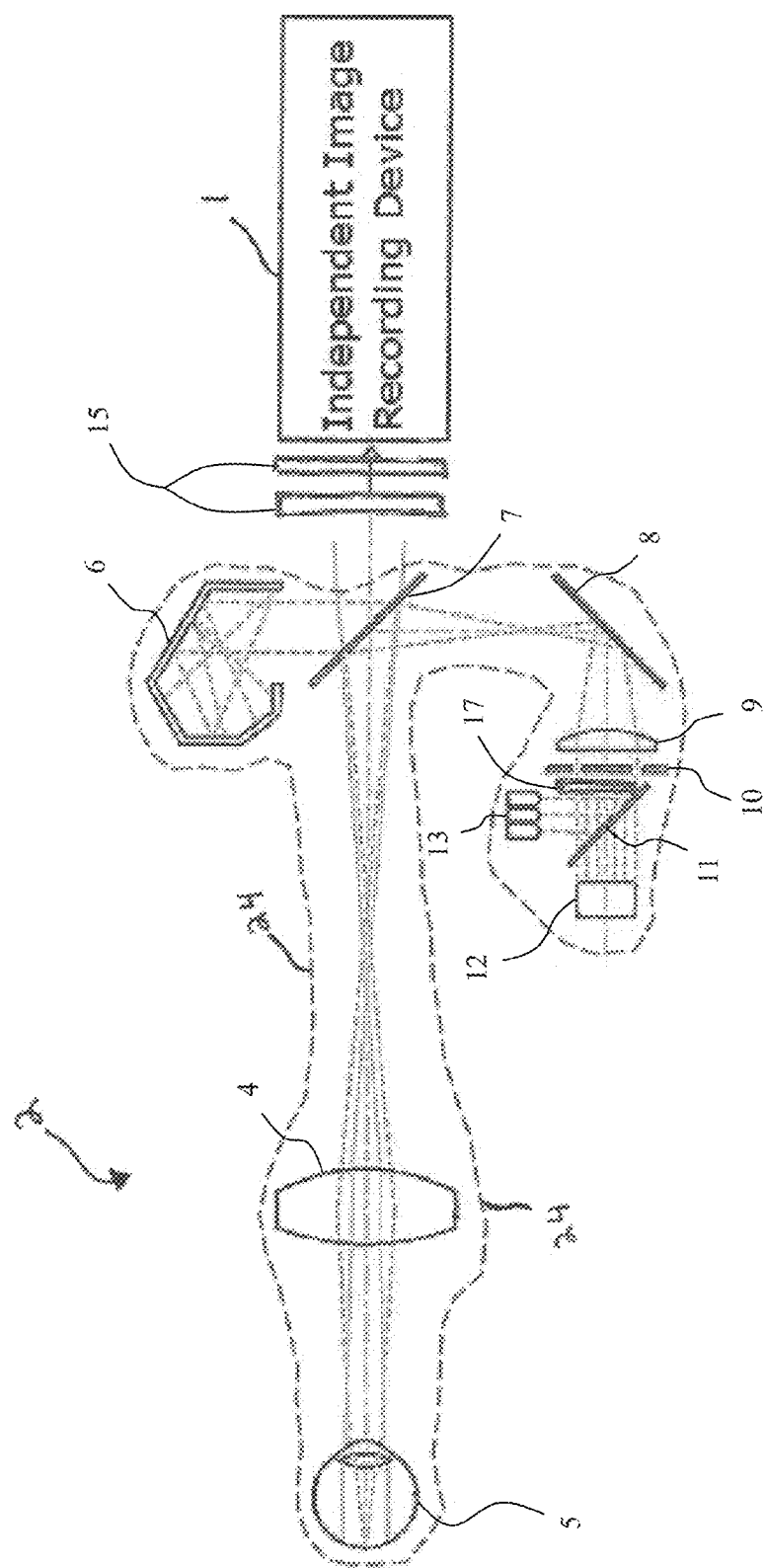
FIG. 2C provides a schematic view of the illumination optical path of an embodiment.
Figure 3:
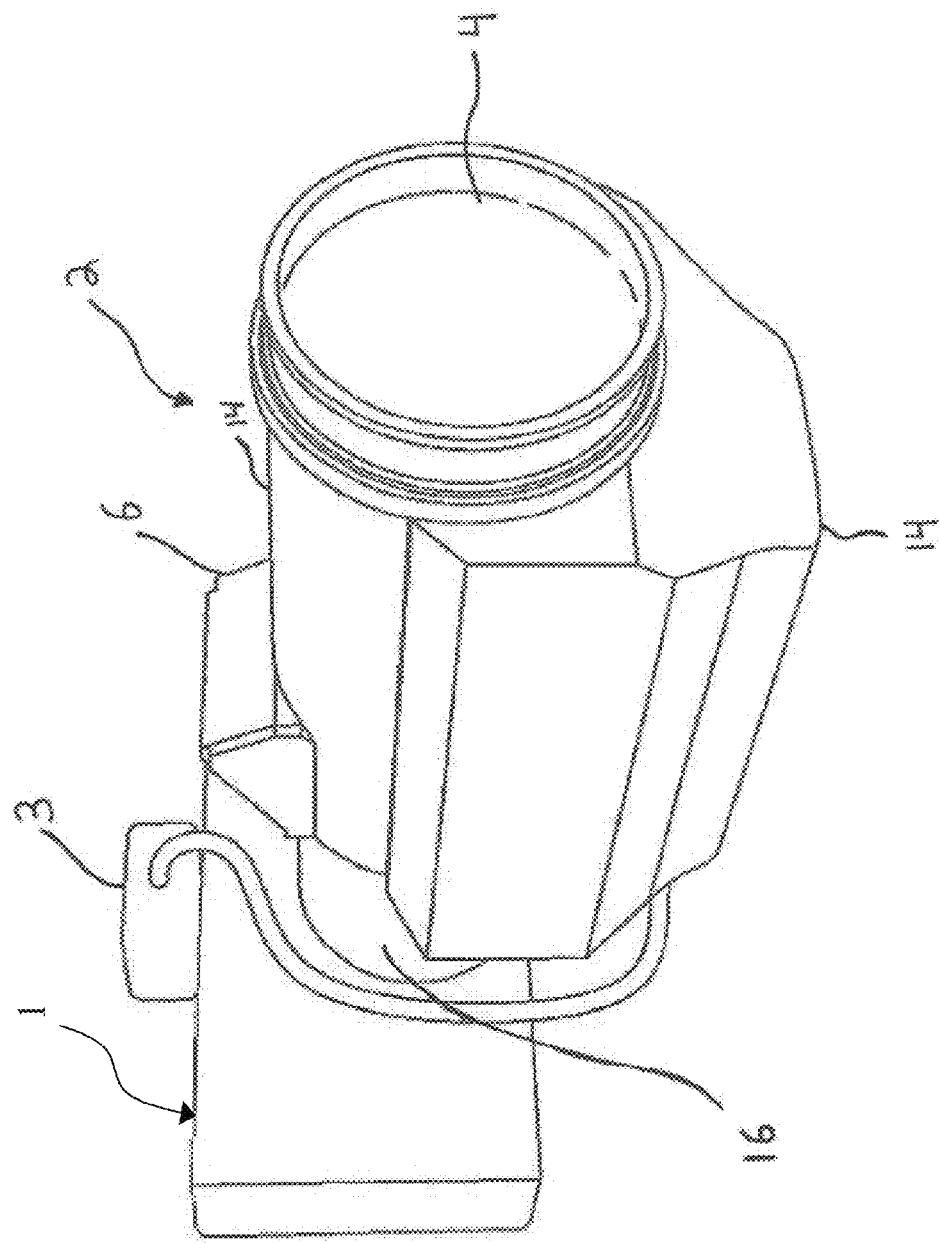
FIG. 3 provides a perspective schematic view of an embodiment showing an external view of a module optical system housing and a view of coupling systems and connection/communication interfaces between a module optical system and an independent image recording device.

FIG. 2C illustrates the illumination optical path 24. As described earlier, the illumination optical path splits into two paths after reaching the beam splitter 7. One path passes into the light trap 6 where it is absorbed and internally reflected. The other branch of the illumination optical path travels along the same path as the module imaging optical path as illustrated in FIG. 2A. Accordingly, in an embodiment of the invention, the illumination optical path and module imaging path are partially shared by means of the location of the beam splitter 7. The novel use of common optical paths allows for simplifying the overall optical paths and reduces total size. Particularly, this simplification greatly reduces the number of optical elements required for imaging the fundus thereby allowing a point and shoot consumer digital camera 1 to be transformed into a stand-alone mydriatic or non-mydriatic portable fundus camera.

Figure 6:
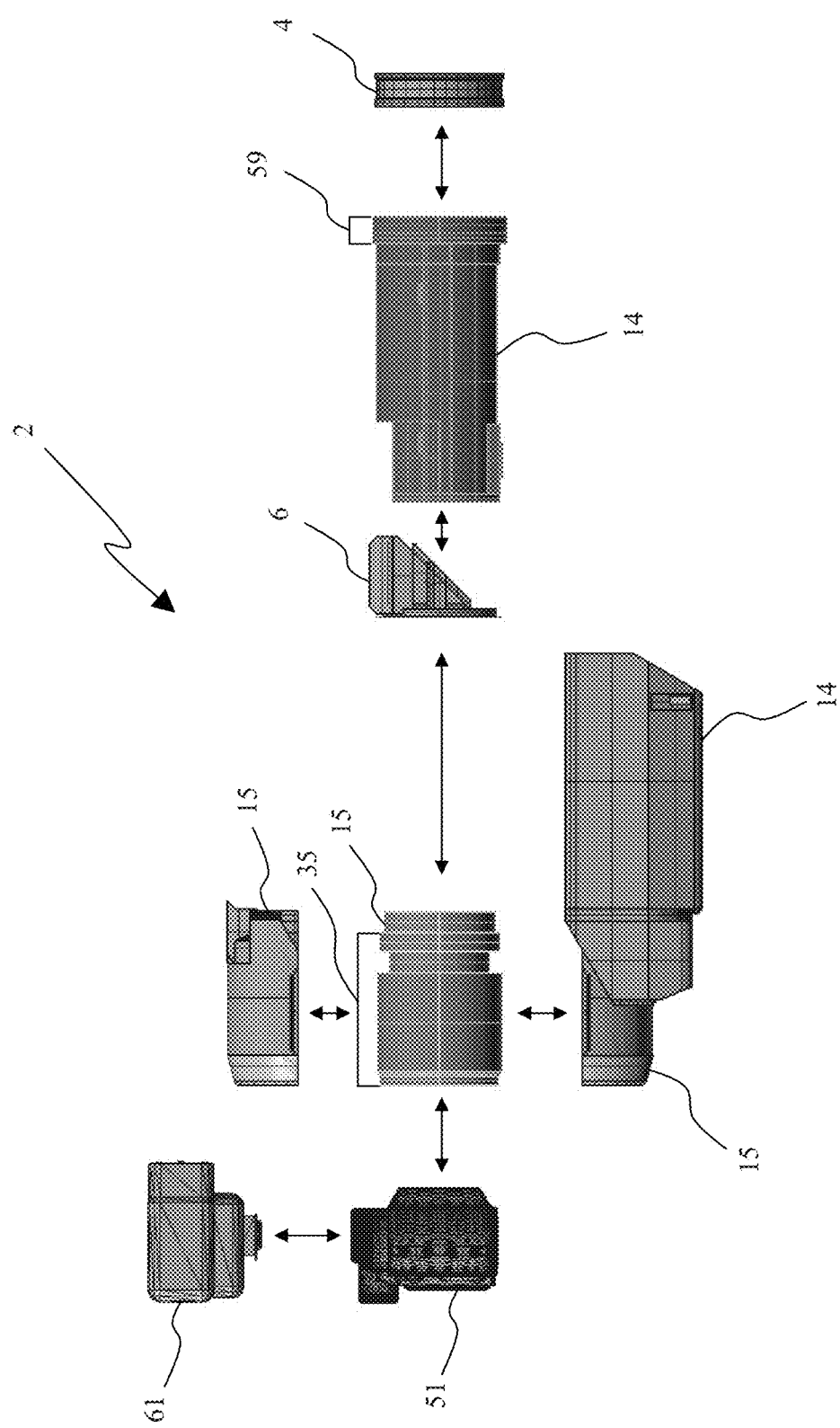
FIGS. 6 and 7 provide 2D and 3D assembly instructions of an embodiment of the portable fundus camera, respectively.
Figure 7:
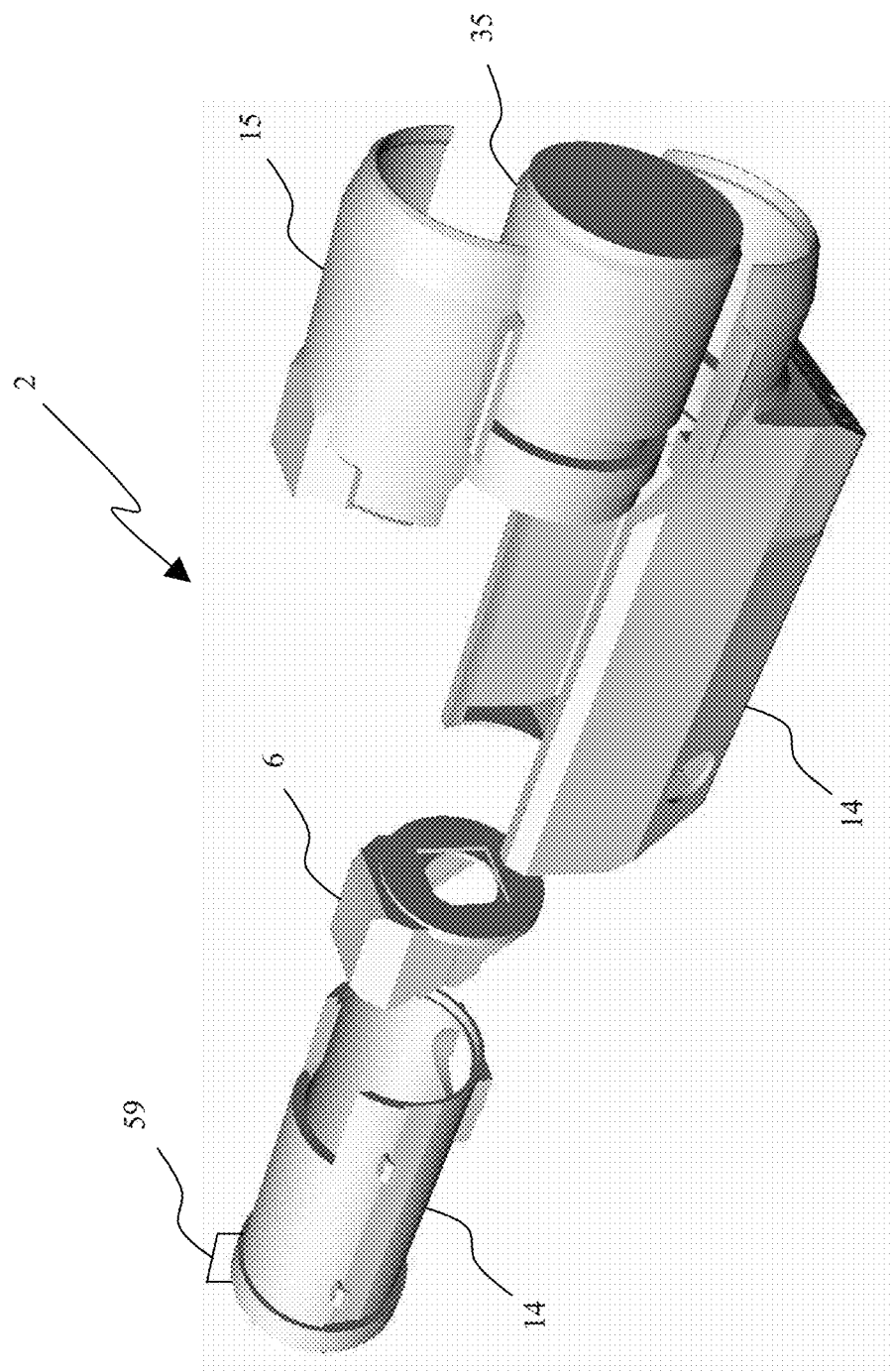

Further, the housing 14 containing the module optical system 2 may be interfaced with the consumer digital camera 1 by means of a module coupling system 15. In an embodiment, the coupling mechanism provides a physical link between the consumer camera 1 and the housing 14, thereby positioning the two components in such a way that the image of the fundus produced by the front objective lens 4 fills the entirety of the image sensor 53. In order to accomplish this, a novel clamping mechanism which incorporates the camera's front lens 35 into the housing 14 is employed. This clamping mechanism holds the camera front lens 35 in such a way that retains the ability of the camera front lens to auto-focus and perform macro-focusing. Further, the camera front lens 35 is held in such a way that holds the focal length of the camera front lens constant, eliminating the need for separate user control of camera focal length. In another embodiment, the housing 14 may have a coupling means 15 which enables the module optical system 2 to be securely attached to the filter adapter ring on many digital cameras. In an embodiment, the overall dimensions of the module optical system 2 attached to the independent image recording device 1 may be roughly 10"×5"×5". Additionally, the housing 14 may also provide a battery pack which can either be AAs, AAAs, or Lithium-Ion rechargeable batteries to provide power to the composing image acquisition illumination observation source 13 and related circuitry thereof. In an embodiment, the housing 14, module optical system 2, consumer digital camera 1 and external flash 61 are assembled in such a way as provided in FIGS. 6 and 7.

Figure 4:
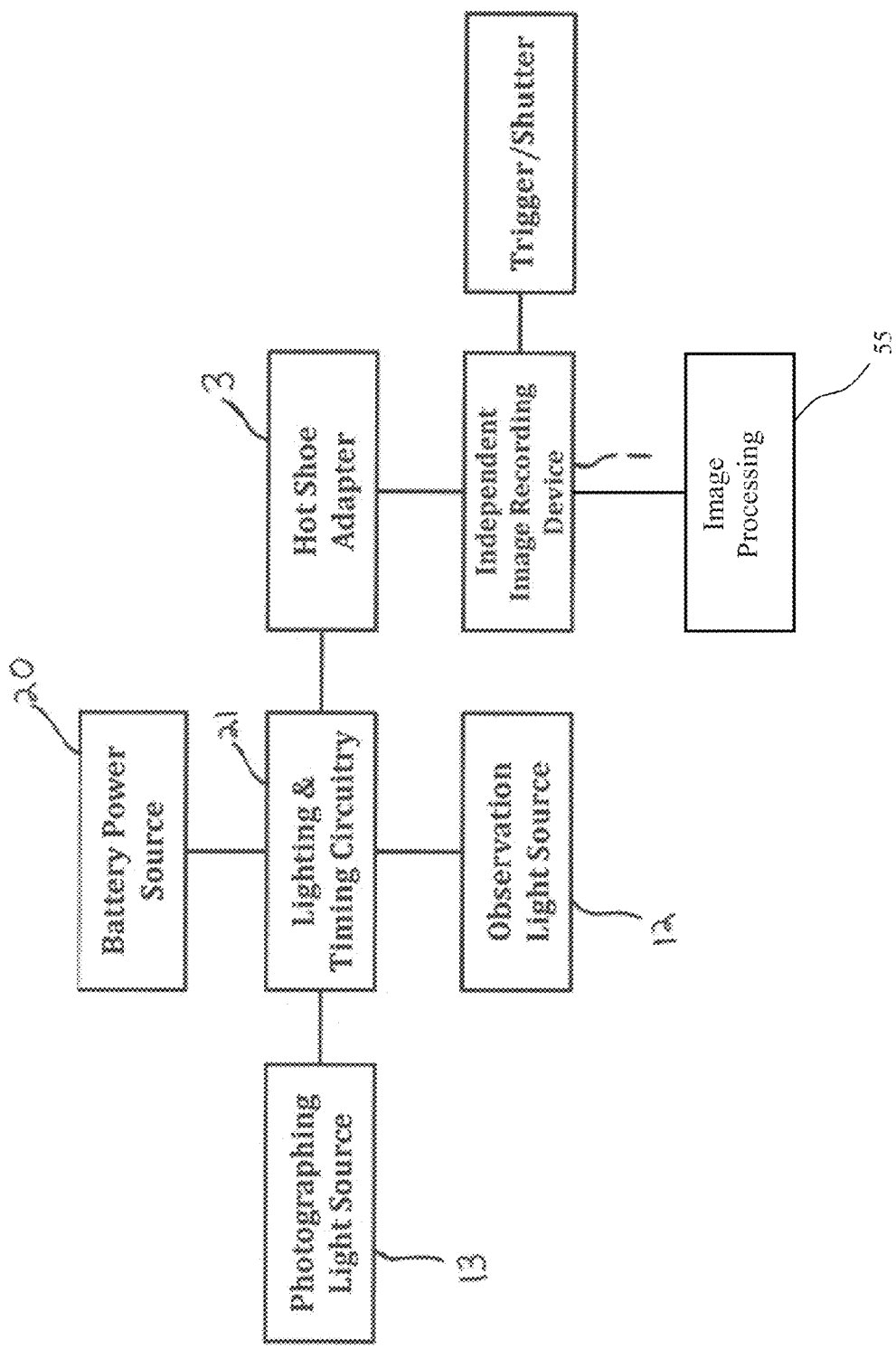
FIG. 4 provides a schematic block diagram illustrating an embodiment of the basic illumination circuitry required for synchronizing the use of the independent image recording device with triggering the photographing illumination in the module optical system.

FIG. 4 illustrates a basic circuitry block diagram of an embodiment of the invention which is used to synchronize the operating of taking a photograph with the consumer camera 1 and triggering the final image acquisition illumination source 13 of the module optical system 2 in order to provide adequate illumination for photographing the fundus. A hot shoe adapter 3 may be connected to the consumer camera 1 and can electrically communicate when the trigger/shutter 22 sequence of the consumer camera 1 once initiated. In this embodiment, the hot shoe adapter 3 is able to notify the light and timing circuitry 21 when the trigger/shutter sequence of the independent image recording device 1 is initiated. At this time, the lighting and timing circuitry 21 may disable the composing light source 13 while triggering the final acquisition light source 13. This enables the module optical system 2 and independent image recording device 1 to be easily integrated so as to enable photographing the fundus using the same simple techniques used for operating an independent image recording device such as a commercial digital camera. The final image acquisition illumination source 12 intensity is 2-5 orders of magnitude higher than the composing image illumination source 13 and furthermore is discharged in a total time of 100-200 ms. Because of this, the relative intensity of the composing illumination is miniscule in compared to the final image illumination and thus is not incorporated into the final image. As such, in an embodiment, the need for this triggering circuitry 21 is eliminated altogether in order to further simplify the device and increase manufacturability.

Furthermore, the final image acquisition illumination source 12, which may be a xenon flash tube, is able to electrically interface with the consumer digital camera 1 through the use of a hot shoe adapter 3 that attaches to the top of the camera. When the shutter button is pressed on the consumer camera device, the consumer camera device 1 sends an electronic signal through the hot shoe adapter 3 and the circuitry of the module optical system 2. This allows for the user to trigger the shutter and fire the illumination instantaneously. This flash coupling also takes advantage of the digital camera's through-the-lens (TTL) metering system, and as such allows for the camera to directly integrate auto-exposure features to the novel optical attachment, thereby simplifying user operation inexpensively.

In one embodiment, the final image acquisition illumination source 12 is provided by an external light source that originates outside of the fundus camera housing. The external light source may be re-routed to the fundus camera housing through a bundle of optical fibers. The distal end of the optical fibers would then act as the final image acquisition illumination source 12.

In another embodiment, the external light source may be comprised of an internal flash 65 built-in to the consumer camera device, or may originate in a separate embodiment from an external flash 61, which mounts to the hot shoe adapter 3 connected to the consumer camera device 2. Further, the external flash may not be connected directly to the consumer camera device, but may be triggered to fire by wireless communication or by firing of the internal flash 65 of the consumer camera device 1. In this embodiment, the external flash device 61 would serve as a slave flash and interface with the consumer camera device 1 through use of either a wireless or flash slave signal. In this embodiment the internal flash of the consumer camera device 1 would fire when the shutter button 22 is pressed, and internal flash 65 would trigger the external flash device 61 to fire simultaneously. Flash intensity would be set manually by the fundus camera user either on the fundus camera housing or ideally on the external flash device itself.

In an embodiment the external flash device 61 would be configured to interface with the consumer camera device 1 by either use of a hot shoe connector 3 or PC cord. This embodiment allows direct control of flash intensity by the consumer camera device 1 to obtain an appropriate exposed photograph of the retina. The consumer camera device 1 would fire a pre-flash by interfacing with the external flash device 61 to allow the image sensor 53 of the consumer camera device 1 to determine flash intensity necessary to obtain an appropriately exposed image of the retina. The consumer camera device 1 would then signal to the external flash 61 to fire a final image acquisition flash to acquire the final image of the retina based on the settings provided by the pre-flash exposure. In an embodiment the timing between pre-flash and final flash exposure would be of a minimum duration necessary to obtain set the appropriate exposure parameters of the external flash, without causing constriction of the pupil of the eye, thereby allowing for non-mydriatic imaging of the retina.

In a further extension of this embodiment, the xenon flash tube for the external flash 61 is placed directly in the housing 14 of the fundus camera and connected to the external flash electrically through an electrical cord 63. This significantly enhances transmission of the light produced by the xenon flash over other embodiments that have been described that utilize fiber optic coupling of the external flash to the fundus camera housing. Further, the direct electrical connection allows the external flash device to precisely control firing of the xenon tube both for initial pre-flash emissions for thru the lens metering and final flash firing for performing final image acquisition with the fundus camera. In an embodiment this electrical cord can be disconnected xenon tube at the site of entry into the fundus camera or at the site of connection to the external flash 61. This allows ease of manufacture, fundus camera disassembly and parts replacement should the external flash device suffer a malfunction and require repair.

Coupling of the illumination pathway thru the front objective lens 4 generates undesired back reflections from the eye 5 and front objective lens 4. Undesired reflections can be reduced through a means of polarizing the illumination light from the fundus camera. A first polarizer 41 is placed in the illumination optical path 24 prior to the beamsplitter 7 and after the image mask 10 and second polarizer 43 is placed in the image acquisition optical path 23 between the beamsplitter 7 and consumer camera device 1.

If the first and second polarizers are placed at orientations of 90 degrees to one another, the back reflections are significantly reduced. This method utilizes the optical principle of cross polarization, whereby polarized light (e.g., P polarized light) striking a reflective surface (e.g. glass, metal) alters the polarization state of reflected light to the opposite state (e.g., S polarized light). The second polarizer oriented at 90 degrees to the first polarizer permits light reflected from the retina that remains P polarized to pass to the consumer camera device, while light reflected from the front objective lens 4 that is the opposite S polarized is blocked. The polarizers can comprise either linear or circular polarizers, dependent on whether the consumer camera device uses contrast based or phase based focusing algorithms respectively, and may be aligned at angles other than 90 degrees to provide variable degrees of rejection of back reflections. The polarizers can be of the wire-grid or thin film type.

In an embodiment, the first 41 and second 43 polarizer may be replaced by a single polarizing beamsplitter. To some degree, this embodiment may be less utilized over separate polarizers given the complexity of manufacture of the polarizing beamsplitter compared to a standard plate beamsplitter 7. To some degree, this embodiment may be less utilized over separate polarizers given light reflected from the entire retina that has changed its polarization state is blocked by the polarizing beamsplitter. This results in a flat retinal image and loss of retinal detail from retinal structures including but not limited to epiretinal membrane, refractile drusen, and the internal limiting membrane.

In an embodiment, separate first 41 and second polarizers 43 are used as specified to improve manufacturability of the fundus camera. Use of separate polarizers permits the back reflection produced by the front objective lens to be specifically blocked from reaching the image sensor of the consumer camera device 1 by adjusting the size and shape of the second polarizer 43 in front of the consumer camera device 1. In one embodiment the second polarizer 43 can cover a limited central area of image sensor 53 of the consumer camera device 1 to block back reflections specifically from the front objective lens 4 while allowing reflected light of all polarization states that are outside of this central limited area to pass to the image sensor of the consumer camera device. The embodiment results in an image that contains both P-polarized and S-polarized light reflected from the retina except centrally.

Figure 10:
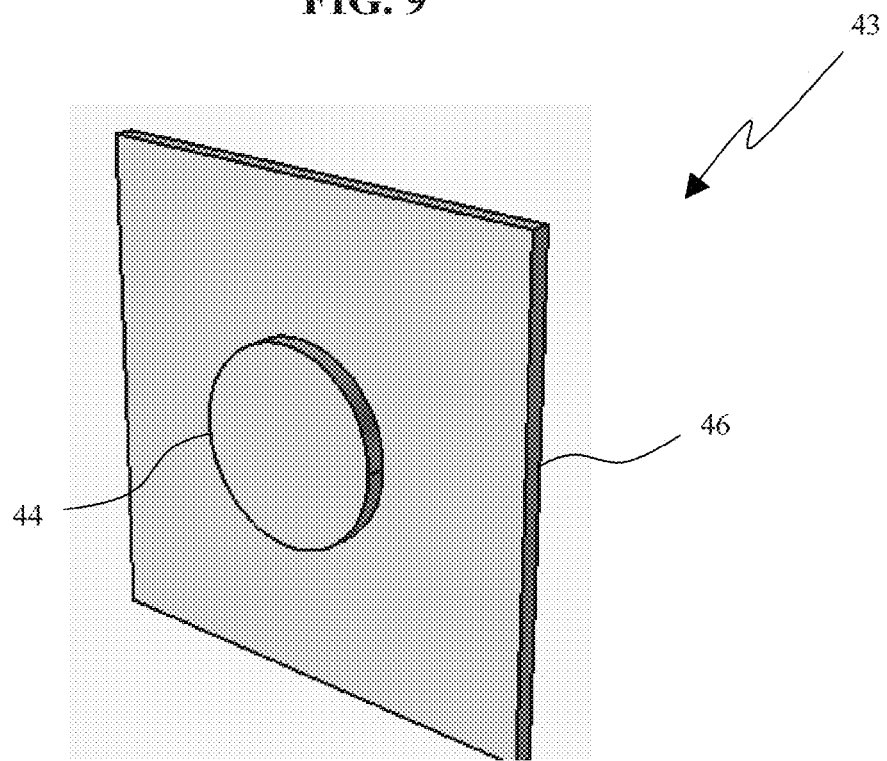

As the second polarizer 43 also functions effectively as a neutral density filter, the final recorded image produced by this embodiment is necessarily darker centrally than peripherally. This image difference in image brightness is easily adjusted with post image processing by the image processing module. In an embodiment, FIG. 10 provides how the second polarizer 43 covering a limited central area can be coupled with either a neutral density filter 46 (or a third polarizer) oriented at a different angle to the second polarizer to adjust the image brightness of the peripheral retina to match that of central retina. This embodiment can eliminate the need for post image processing by the image processing module 55 while retaining peripheral P-polarized and S-polarized light to maintain full retinal detail. The neutral density/third polarizer 43 can be separated from the second polarizer by a variable distance or they can be placed together with the second polarizer inserted into a hole created in the center 44 of the neutral density/third polarizer.

In an embodiment of the present invention, the image sensor 53 of the consumer digital camera 1 may have to be modified to increase the sensitivity to infrared wavelengths to allow for effective non-mydriatic imaging. All consumer cameras come pre-installed with an infrared blocking filter 69 in front of the image sensor. In order to enable non-mydriatic imaging, this filter must be removed and replaced with a full-spectrum clear glass filter to allow for imaging in the 400 nm to 1200 nm wavelengths. This modification can be made either during the manufacturing process of the digital camera itself, or post production. Although the composing illumination source 13 consists of infrared light in the mydriatic case, the final photograph taken does not record any wavelengths in the infrared range. This is accomplished by adding an infrared blocking filter 67 and heat absorbing glass 31 in front of the final image acquisition illumination source 12. By moving these infrared blocking filters from in front of the imaging sensor 53 to in front of the illumination source 12, infrared light contaminations in the final image can be eliminated without the need for mechanical flip mirrors, etc. In an embodiment of the non-mydriatic case, a cold mirror filter 11 is employed to separate the composing illumination source 13 from the final image acquisition illumination source 12. This ensures that when a photograph is taken, the cold mirror blocks any infrared light from the composing light source 13 and therefore only visible light is used for taking the photograph. Furthermore, by taking advantage of the IR/visible light exposure ratio when the photograph is taken, no additional circuitry is required to communicate between the infrared composing illumination 13 and the final image acquisition illumination 12. A camera's exposure time (set at $\frac{1}{640}$s for example) only allows a fraction of the infrared composing light 13 to be captured by the imaging sensor 53. In contrast, the $\frac{1}{640}$s exposure time is more than enough to account for nearly 100% of the visible light outputted from the external flash 12/61 which can fully discharge on the order of $\frac{1}{2000}$s. The combination of these two temporal characteristics of the light output causes the IR/Visible ratio in the final image to be virtually null, thereby simplifying the manufacturing process of the portable fundus camera.

It should be noted that this aspect of the embodiment of allows for the portable fundus camera to use the same imaging sensor 53 for both observation and photographing the fundus of the eye in the non-mydriatic case. This allows both the composing and final image acquisition image sensors to be incorporated within the consumer camera 1 and eliminates the need for separate imaging elements. The need for two separate photoelectric imaging elements increases the total size of the system. In brief, this feature may allow for simplification of the non-mydriatic optical and imaging system by taking advantage of the IR/visible light exposure ratio when the photograph is taken. The light output causes the IR/Visible ratio in the final image to be virtually null, resulting in a design that allows for the use of a consumer digital camera 1 in combination with the module optical system 2 for both observing and photographing the fundus at a very low cost.

The consumer camera device in one embodiment has a built-in display unit for composing and focusing (e.g. Liveview) as well as reviewing the digital image of the retina that has been acquired and stored in the device. In an embodiment this display consists of a liquid crystal display (LCD) 51 and is further comprised of a display that can be positioned at multiple orientations relative to the camera body (e.g. flip screen). In an embodiment the orientation of the screen can be rotated 180 degrees in both vertical and horizontal orientations to provide a mirror image display relative to its usual position on the camera body.

Some consumer camera devices possess a rotatable LCD capability as an inherent feature of the device (e.g. Canon G11). These cameras are able to detect when the LCD 51 has been placed into a mirror orientation (e.g., through a digital switch) and through software processing are able to digitally flip the displayed image sensor of the consumer camera device so that the user sees the usual and correct orientation of the image on the image sensor 53. In an embodiment, this capability for detecting the LCD has placed into a mirror orientation is disabled (e.g., through removal of the digital switch). As the camera is not able to detect that the LCD 53 is in a mirror orientation, the image from the image sensor is now displayed in a mirror orientation.

The front objective lens 4 of the fundus camera produces an image of the retina that is in a mirror orientation. Thus, when displaying this image on the LCD 53, if the LCD were left in its usual position, the user would see a mirror orientation of the retina. This can potentially confuse the user as movement of the camera to the left will result in the image moving to the right, and similarly movement of the camera to the right will result in the image moving to the left. By flipping the LCD 53 into a mirror orientation, the combination of mirror LCD orientation and mirror retinal image orientation cancel one another to produce an image of the retina on the LCD that is now in a non-mirrored orientation. Thus, when the user moves the camera to the right, the image on the LCD will now move to the right, and when the user moves the camera to the left, the image on the LCD will now move to the left. This embodiment allows the user to more easily align the camera with the eye when looking at the LCD by using movements that are more natural to them.

Additionally, in an embodiment, the settings for the consumer digital camera 1 may be present during the manufacturing process using the user-definable custom settings programs already built into the camera. Various aspects such as the focal length, initial focus, autofocus, manual focus, white balance, noise reduction, image stabilization, contrast, sharpness, aperture, ISO, and shutter speed may all be pre-set to simplify operation of the device. This allows for the user to operate the camera and produce a successful retinal image by just "pointing and shooting." It should be appreciated that these settings may be programmed into the camera permanent memory, and can only be changed by manually resetting the camera through the menus system. Losing power will not erase these important settings.

In an embodiment, operation of the portable fundus camera will consist of the user turning on the consumer digital camera and also turning on a switch to power the module optical system located on the housing 14. The user may now aim the camera toward the patient's eye. The live view LCD screen 51 on the digital camera will show in real time the image of the patient's fundus and also gives a sense of where the camera most be moved in order to center it on the pupil. When the image is composed, the LCD screen 51 on the camera will show a preview of the fundus image. The user will find a suitable focus point (such as a vessel or the optic nerve) and half depress the shutter to auto-focus the camera. If auto-focus cannot be achieved, the user can switch the camera into its manual focus mode and achieve proper focus by that means. Once focusing is completed, the user can now depress the shutter button completely. This will trigger the hot shoe adapter 3 to fire off the photographing light source 13 in the module optical system 2 to properly expose the image. In an embodiment, the shutter speed chosen for image capture was set to $1/500$s to eliminate motion blur of both the user as well as the patient's eye. The LCD 51 will now show a review of the previously taken image. If the user is not satisfied, he or she may delete the picture and repeat the process again. Exposure levels can also be adjusted by varying the flash power in small increments by means of a switch on the attachment.

In an embodiment, accurate patient identification can be achieved by taking the picture of a patient ID card before any pictures of the retina are taken. In this way, the image files will run in series and correspond to a new patient whenever a picture of a patient ID card exists. The images taken may be stored on the memory card for later clinical use by a certified and licensed medical practitioner. The memory card can be hooked up to wirelessly and automatically uploaded into an archiving system as well through the use of a WiFi enabled SD card (EyeFi) or the like. Telemedicine practices may be used where the images taken will be reviewed by ophthalmologists in a remote location. If the image shows that the patient has a disease or defect, the patient can then be referred to a specialist for more testing and treatment.

In an embodiment the fundus camera will have an additional image processing module to enhance the capability of the camera to perform composing and focusing of the image of the retina as well as enhance the final image of the retina recorded by the consumer camera device. In one embodiment, the image processing module is contained within the consumer camera device 1 and is interface with the user of the fundus camera through the LCD screen 51 of the consumer camera device. In another embodiment, the image processing module is contained as a separate device outside of the fundus camera. In an embodiment image processing is performed by the image processing module at either the local or remote location to which the fundus camera transmits its stored images of the retina.

The image of the retina formed by the front objective lens 4 of the fundus camera is in a mirror orientation. In an embodiment, the fundus camera image processing module will flip the image on the image sensor 53 of the consumer camera device in both horizontal and vertical axes and display the resultant non-mirror image on the LCD of the consumer camera device. In another embodiment, the image recorded by the consumer camera device retains its mirror orientation. A local or remote image processing module of the fundus camera is able to flip the image of the retina recorded by the consumer camera device along both horizontal and vertical axes to display the correct orientation of the retina to the user reviewing the recorded images.

In another embodiment, the image processing module of the fundus camera is able to digitally remove back light reflections recorded by the image sensor of the consumer camera device 1. This removal can be accomplished by a suitable software algorithm that can detect these back light reflections and then remove them digitally from the recorded image. In one embodiment this software algorithm is able to detect the back light reflection by differences in the optical properties of the reflections by one or more of the following: spectral wavelength content, size, brightness, contrast, or hue of the reflection compared to the optical properties of the remainder of the recorded image. In one embodiment of the software algorithm, the algorithm and related computer logic code is able to subtract the content of the back light reflection and retain the content of the retinal image underlying the back light reflection.

In an embodiment, the spectral content of the back light reflections is used to identify the position and size of the reflections in the recorded retinal image. The light reflected from the retina contains primarily green and red spectral components, while the back light reflected from the front objective lens contains spectral content primarily in the blue and green part of the visible spectrum. By specifically analyzing the blue channel of the retinal image, the spectral content of the back light reflection can be identified and used to construct an image mask. The relative spectral signal of the back light reflection can then be combined with the image mask to digitally subtract the back light reflection from the stored retinal image to recover the spectral content of the retina that underlies these reflections—FIG. 11

In a separate embodiment, multiple recorded images of the retina from the consumer camera device can be used by the software algorithm to construct a final image in which the back light reflections are removed. The back light reflections can be identified by spectral content, location, size, brightness, hue as previously specified. Once the back light reflections are identified on each recorded image, the recorded images are then combined by the software algorithm. In locations, where images overlap with one another, the software algorithm chooses to retain the image content from images that do not have identified back light reflections in these location. In other locations where images overlap and there is no back light reflection, the software algorithm chooses the image content to be displayed through another evaluation (e.g., the image with the best contrast) or by averaging the content of the two images where they overlap.) The software algorithm will be able to correctly align and blend the content of the two images by using similar landmarks in each image (e.g. patterns of blood vessel or location of optic nerve). Thus, the final combined image produced by the software algorithm does not contain any back light reflections and is a blended composite of the multiple images.

In one embodiment of the fundus camera a central polarizer is used to remove the central back light reflection produced by the front objective lens of the fundus camera. This configuration of polarizer is advantageous because it removes the central back light reflection while retaining the image of the retina that underlies the central back reflection. Further, this configuration of polarizer preserves the retinal reflections/details from the remainder of the image field except over the central part of the image. The resultant image in practice may have mild changes in brightness and contrast over the central part of the image corresponding to size and location of the polarizer. In one embodiment of the image processing module this mild imbalance is automatically corrected by the appropriate software algorithm. The resultant image following digital correction of central white balance has equivalent white balance over the full extent of the image, enhancing the recorded image produced by the fundus camera. In one embodiment this digital correction is performed in the consumer camera itself. In another embodiment this digital correction is performed following local or remote transmission of the recorded image from the fundus camera.

In an embodiment the fundus camera will contain a transmission module to communicate the images to either a local workstation or to a remote location for image review and diagnostic assessment. This transmission module may be included in the fundus camera housing 14 or be a separate module from the fundus camera housing. The transmission module may connect either locally or remotely by use of a wired or wireless connection (e.g. a cord connecting from the fundus camera to a local laptop computer for image review). In an embodiment, the images are communicated wirelessly through either radio frequency, bluetooth, a cellular or wireless network. The images are transmitted locally and to a remote location for independent archiving outside of the fundus camera itself.

In an embodiment, a data storage card (e.g., SD flash memory card) is used to store images for the consumer camera device. This data storage card has the capability of both data storage and wireless transmission of these stored images both locally and to a remote location. One particular enumeration of the data storage and wireless transmission device would be a commercially available Eye-fi card. The local and/or remote location consists of device (e.g. computer) that archives the stored images from the consumer camera device. Multiple embodiments may comprise this device but it is generally understood to include at least one of the following: a user, a processor, a display, a database, an archive, or any combination thereof. Beyond archival of the stored images on the consumer camera device, the transmission module would allow for communication of images of the fundus to be reviewed for potential pathology by skilled practitioners (e.g. ophthalmologists or optometrists) at a remote location.

Figure 11A:
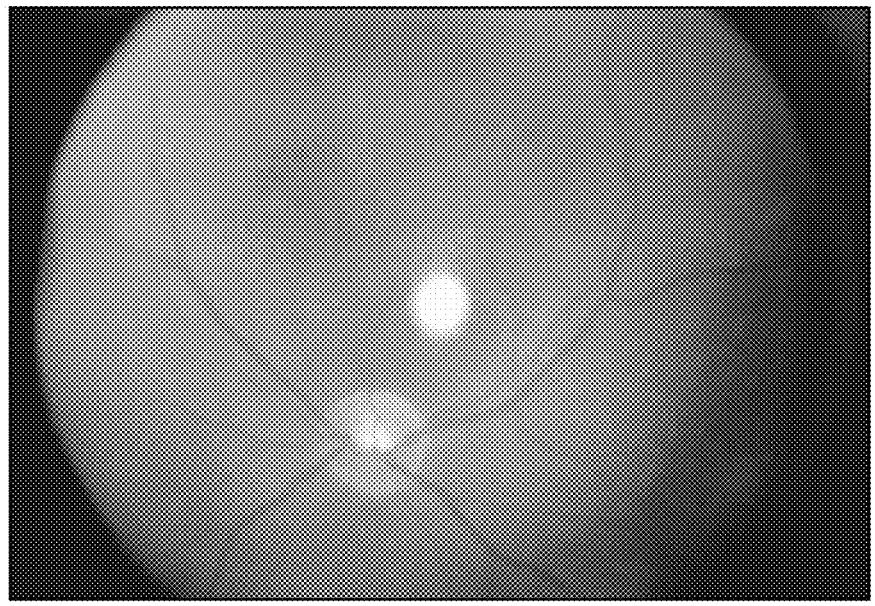
FIG. 11A provides a recorded retinal image prior to digital subtraction of back light reflections.
Figure 11B:
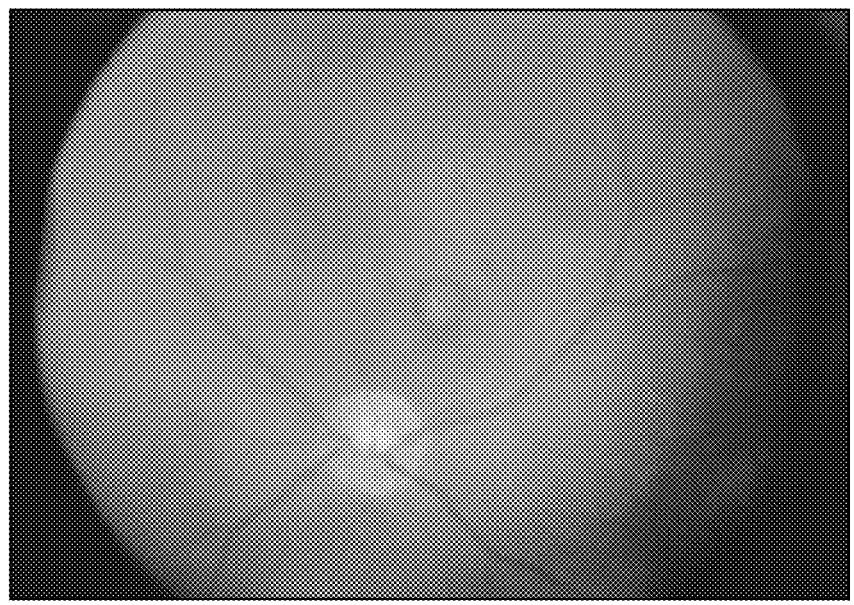
FIG. 11B provides a recorded retinal image after digital subtraction of back light reflection.

FIG. 11 illustrates the effect of the digital subtraction of spectral content of back light reflections practicing an embodiment of the present invention. FIG. 11A provides a recorded retinal image prior to digital subtraction of back light reflections. FIG. 11B provides a recorded retinal image after digital subtraction of back light reflection.

FIG. 12 illustrates the effect of the digital subtraction of back light reflections by combining multiple images practicing an embodiment of the present invention. Retinal image no. 1 (FIG. 12A) is combined with retinal image no. 2 (FIG. 12B) to provide a combined image (FIG. 12C).

Figure 13A:
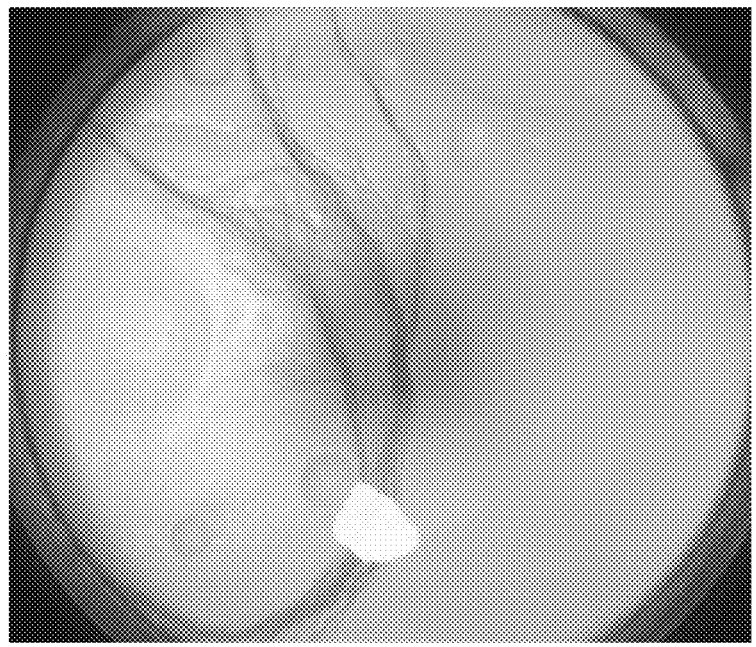
FIG. 13A provides a recorded retinal image prior to digital enhancement of central white balance.
Figure 13B:
FIG. 13B provides a recorded retinal image after digital enhancement of central white balance practicing an embodiment of the present invention.

FIG. 13 illustrates the effect of digital enhancement of central white balance practicing an embodiment of the present invention. FIG. 13A provides a recorded retinal image prior to digital enhancement of central white balance. FIG. 13B provides a recorded retinal image after digital enhancement of central white balance practicing an embodiment of the present invention.

Figure 14A:
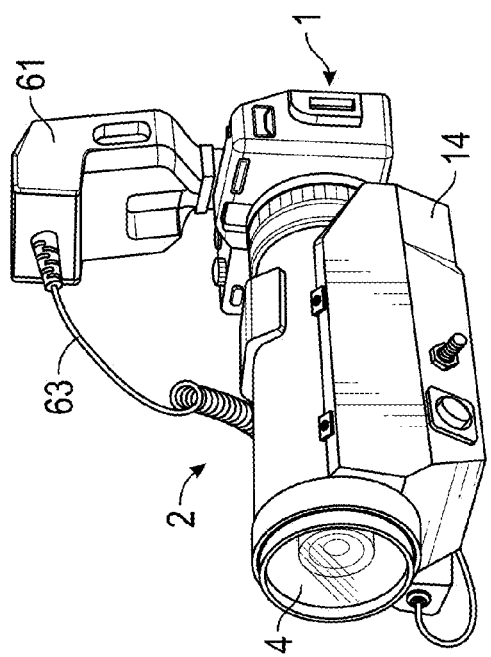
FIG. 14A illustrates an embodiment using a Canon G10 consumer camera device.
Figure 14C:
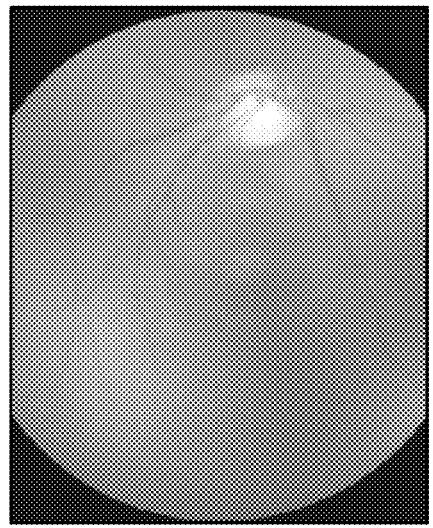
FIG. 14C illustrates practicing a non-mydriatic embodiment using the Canon G10 consumer camera device on a human eye.
Figure 14B:
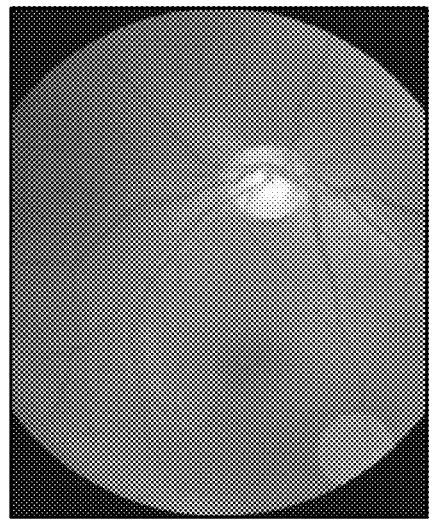
FIG. 14B illustrates practicing a mydriatic embodiment using the Canon G10 consumer camera device on a human eye.

FIG. 14 illustrates practicing an embodiment of the present invention. FIG. 14A illustrates an embodiment using a Canon G10 consumer camera device. FIG. 14B illustrates practicing a mydriatic embodiment using the Canon G10 consumer camera device on a human eye. FIG. 14C illustrates practicing a non-mydriatic embodiment using the Canon G10 consumer camera device on a human eye.

FIG. 15A, FIG. 15B, and FIG. 15C illustrate practicing an embodiment of the present invention. FIG. 15A and FIG. 15B illustrate an embodiment using a Panasonic Lumix G2 consumer camera device. FIG. 15C illustrates the resultant fundus image practicing a mydriatic embodiment.

In summary, an aspect of an embodiment or various embodiments of the present invention comprises, among other things, a novel and very low-cost portable fundus camera. An aspect of various embodiments of the present invention may provide a number of novel and non-obvious features, elements and characteristics, such as but not limited thereto, the following: the system may rely on a consumer digital camera to capture the image of the fundus, conduct the focusing, trigger the illumination light, provide image stabilization, and enable in-depth user control. The novel portable fundus camera has the ability to take non-mydriatic images of the fundus. In addition, an aspect of an embodiment of the present invention comprises the ability for the system to be completely battery powered and operated. There will not necessarily by a cord or connection to conventional external power supply. Furthermore, the system will not require the existence of a separate eyepiece (necessarily) for user viewing and composition of the fundus image. Accurate composition and focus may be achieved from the electronic Live-View screen of the digital camera. Additionally, through the use of infrared and visible spectrum LED technology in addition to a xenon flash unit, an aspect of embodiments of the present invention provides that the portable camera will be able to function as a non-mydriatic camera.

An aspect of one or various embodiments of the present invention may provide a number of advantages, such as but not limited thereto, the following:

True Portability—

Other cameras require a dedicated, wired power source. An embodiment of the present invention may be, for example, be operated by AA/AAA batteries in addition to the lithium battery supplied with the digital camera. This provides a distinct advantage, primarily in allowing for clinicians to diagnose patients in remote screening locations in developing countries as well as improving workflow when one must move from exam room to exam room.

Ease-of-Use—

Because an embodiment of the camera may use a consumer digital camera as its base, operation of the camera will come easily and naturally to most users. With a brief 5 minute introduction on how to operate the camera, for example, untrained medical staff will be able to obtain clear, accurate images of a patient's retina. In contrast, fundus cameras currently on the market require a trained retinal photographer to operate.

Low Cost—

An embodiment of the present invention may be able to be marked at a fraction of the cost of similar products on the market. This will financially enable smaller clinics in the US as well as well as practitioners in developing nations to provide adequate screening opportunities and thus reduce cases of preventable blindness worldwide.

High Resolution Images—

In an embodiment of the camera, through the use of the digital camera sensor, as aspect of an embodiment of the invention will also provide the ability to take pictures up to 15MP, for example. Other "portable" fundus cameras only have a resolution of 2MP.

EXAMPLES

Practice of an aspect of an embodiment (or embodiments) of the invention will be still more fully understood from the following examples, which are presented herein for illustration only and should not be construed as limiting the invention in any way.

Example Set No. 1

Referring to the figures throughout, an aspect of an embodiment of the present invention provides a hand-held portable fundus camera system. The hand held fundus camera system may comprise: a module optical system [2] capable of being integrated with a consumer camera device [1] for auto focus photography by the consumer camera device of the fundus of an eye [5]. The module optical system [2] may comprise: a composing image acquisition illumination observation source [13] (e.g., photographing light source); a final image acquisition illumination source [12] (e.g. observation light source); an optical separator and transmitting means [33] (e.g., IR filter [67], heat absorbing glass [31], cold mirror/beam splitter [11] or the like) for separating and transmitting the composing image acquisition observation illumination source [13] and the final image acquisition illumination source [12] to an image mask [10], of which is relayed to the retina of the fundus through the use of a redirecting mirror [8], a beam splitter [7] and a front objective lens [4]. The image mask [10] may be configured to provide light that illuminates the retina to output an image that is relayed through the objective lens [4] and captured by the consumer camera [1] to provide an image of the retina [5]. Also included is a module interface system [15] (e.g. macro lenses, physical couplings, macro extension ring) to integrate the module optical system [2] with the consumer camera device [1]. It should be appreciated that the module interface system [15] enhances the macro focusing capability of the consumer camera device [1] to enable auto-focus photography by the consumer camera device [1] of the fundus image produced by the front objective lens [4].

The image mask [10] may configured to create a bundled donut of light. The module optical system [2] may further comprise a diffuser [17]. The module optical system [2] may further comprises a rear converging lens [9]. The rear converging lens [9] optically couples an illumination optical path [24] to an imaging acquisition path [23]. The module optical system [2] may further comprise a light trap [6] disposed above the beam splitter [7] whereby light passing through the beam splitter [7] along the illumination optical path [23] and not redirected along the module imaging optical path [24] is absorbed by the light trap [7]. The light trap [6] may be lined with at least one of light absorbing material, black absorbing felt, absorbing neutral density filter, or any combination thereof. The light trap [6] may further comprises walls which cause light to reflect internally within the light trap [6]. The fundus camera may further comprises a housing [14] that comprises the module optical system [2] and configured to couple the module optical system [2] to the consumer camera device [1]. The housing [14] may be configured provide an optical barrier that separates the illumination optical path [24] from the imaging acquisition optical path [23] except between the beam splitter [7] and the redirecting mirror [8] of the illumination optical path [24]. The housing [14] may be configured to allow detachment of the illumination optical path [24] from the imaging acquisition optical path [23] to enhance manufacturability and maintenance of the fundus camera. In an approach, distance between the front objective lens [4] and the rear converging lens [9] and the image mask [10] is optimized to reduce back-reflections while still providing adequate illumination of the retina. The size, position, and focal length of the rear converging lens [9] in combination with the front objective lens [4] focuses the bundled donut of light created by the image mask [10] posterior to the cornea. The composing image acquisition illumination observation light source [13] may comprise a visible light source. The visible light source [13] may be comprise an LED. The visible light source [13] may comprise a white, red, green, or blue LED or a combination thereof. The blue LED provides a wavelength capable of exciting fluorescein dye for fluorescein angiography. The final image acquisition illumination source [12] may comprise a xenon flash bulb. The final image acquisition source [12] further comprises a reflector for the xenon flash bulb. The beam splitter [7] may comprise a standard 50 percent reflection and 50 transmission mirror. The beam splitter [7] comprises a less than 50 percent reflection and greater than 50 percent transmission mirror to enhance transmission of the image of the retina produced by the front objective lens [4] to the consumer camera device [1]. The beam splitter [7] comprises either at least one of dichroic filter, bi-dichroic, or triple dichroic filter, or any combination thereof. The beam splitter [7] may comprise a red, green, blue triple dichroic. The beamsplitter [7] reflects blue light configured for exciting fluorescein dye and transmits the resulting reflected light from the eye to the consumer camera device [1]. The housing [14] encloses module optical system [2] and may be configured to couple the module optical system [2] to the consumer camera device [1]. The housing [14] may further comprises electrical circuitry to interface the module optical system [2] with the consumer camera device [1]. The housing [14] may further comprises a battery-based power source [20]. The housing [14] may be in communication with or dispose to the module interface system [15], having a mount for the front camera device lens [35] of the consumer camera device [1] to maintain the front camera device lens [35] at a constant focal distance for focusing on the image of the retina produced by the front objective lens [4]. The module interface system [15] may further comprise a macro extension ring, the macro extension ring being integrated into the housing [14] of the fundus camera (e.g., to enhance manufacturability of the fundus camera). The module interface system [15] may further comprise a macro lens [37] and/or a macro extension [39] to enhance the consumer camera device's [1] ability to focus on the image of the retina produced by the consumer camera device [1]. The consumer camera device [1] comprising a front camera device lens [35], wherein the macro extension ring is positioned to place the central focal point of the camera device front lens [35] at the location of the image formed by the front objective lens [4] (thereby enhancing ability of the consumer camera to use its entire focal range both positive and negative to allow it to focus on patients with a range of eyeglass prescriptions). The module interface system [15] may further comprise a macro lens to enhance the consumer camera device's ability to focus on the image of the retina produced by the consumer digital camera device [1]. The consumer camera device [1] may comprising a front camera device lens [35], wherein the macro lens is positioned to place the central focal point of the camera device front lens [35] at the location of the image formed by the front objective lens [4] (thereby enhancing ability of the consumer camera to use its entire focal range both positive and negative to allow it to focus on patients with a range of eyeglass prescriptions). The consumer camera device [1] may further comprise at least one of: auto-focusing elements; auto-exposure elements; image stabilization technology; means for taking macro images; LCD for observing the image of the retina; flash illumination for enhancing image recorded by the consumer camera; or data storage system for recording of the image of the retina (or any other system, device, composition, material, computer program logic, computer processing, or component as desired or required). The data storage system may further comprise a flash memory device for storing images of the fundus. The fundus camera may further comprise a transmission module for communication to a local and/or remote location. The transmission module may further comprise a network enabled wireless data transfer system with means for transferring recorded images of the fundus [5] to an independent archival system. The transmission module may further comprise a combination data storage device and wireless data transfer system. The combination data storage device and wireless data transfer system may further comprise an Eye-fi card or the like. The local and/or remote location may be at least one of a user, a processor, a display, a database, an archive, or any combination thereof. The transmission module may provide a means, system or mechanism for the communication of images of the fundus [5] to be reviewed by ophthalmologists or care provider in a remote location. The fundus camera may further comprise an LCD screen (or other type of displays as desired or required), whereby the LCD screen [51] may be configured to show a live image of the image on an image sensor [53] of the consumer camera device [1]. The LCD screen [51] may be a flip screen type comprising a rotation mechanism configured to allow inversion of horizontal and vertical axes of the flip screen LCD [51]. The flip screen [51] may further comprise the capability to display a mirror image display of the image on the image sensor [53] of the consumer camera device [1] to enhance ease of alignment of camera with the patients eye. The fundus camera may further comprise an image processing module [55], wherein the consumer camera device comprising an image sensor [53]. The image processing module [55] may be configured to enhance the image of the retina recorded by the image sensor [53] of the consumer camera device [1]. The image processing module [55] may be configured to display a mirror image of the image of the retina on the image sensor [53] of the consumer camera device [1]. The image processing module [55] may be configured to eliminate back light reflections from the image of the retina recorded by the image sensor [53] of the consumer camera device [1]. The elimination of back light reflections identifies the back light reflections from the retinal image recorded by the image sensor [53] of the consumer camera device [1] by comparing the optical properties of the back light reflections with the optical properties of the retinal image. The optical properties may include spectral content, size, brightness, and/or contrast. The image processing module [55] may be configured to subtract the optical properties of the back light reflections with the optical properties of the retinal image to remove the back light reflections and restore the retinal image that is obscured by the back light reflections. The image processing module [55] may be configured to combine overlapping images of the retina recorded by the consumer camera device [1], wherein the back reflection is removed from the final combined image by choosing areas of each individual image that do not include the optical properties of the back reflections. The image processing module [55] being configured to store a mirror image of the image from the image sensor [53] of the consumer camera device [1] to correct the inverted orientation of the image from the image sensor [53] of the consumer camera device [1]. The image processing module [55] may be configured to adjust the exposure of the recorded image of the consumer camera device [1] to even the illumination across the image recorded of the consumer camera device [1]. The front objective lens [4] may be a double aspheric lens, an aspheric convex lens, a convex-convex lens, or a convex-plano lens (or as desired or required). The front objective lens [4] may have antireflection coatings to reduce illumination source reflections. The front objective lens [4] may be a standard lens normally used for indirect opthalmoscopy. The front objective lens [4] may have an effective power of about 20D to about 22D (e.g., Volk Digital Clearfield lens Ocular Instruments OI-22M lens) to provide about 50° field of view of the fundus [5]. The front objective lens [4] may be secured by a lens mount [59] with a front converging lens mask that is configured to reduce edge image artifacts from the front objective lens [4]. The fundus camera may further comprise a polarizer means, system, device for polarizing light to reduce back light reflections from the fundus camera [2]. The polarizer means may comprise a first polarizer [41] that may be placed in the illumination optical path [24] and a second polarizer [43] is placed in the image acquisition optical path [23]. The first polarizer [41] and the second polarizer [43] may be oriented at different angles relative to one another (or as desired or required). The first polarizer [41] and the second polarizer [43] may be oriented at about 90 degrees to one another to enhance cross polarization to reduce back light reflections from the fundus camera [2]. The first polarizer [41] and the second polarizer [41] may be placed after the image mask [10] and between the beamsplitter [7] and the front lens [35] of the consumer camera device [2]. The second polarizer [43] may comprises a circle [44] of dimensions needed to cross polarize only the reflection from the front objective lens [4] to reduce back light reflections from the front objective lens [4]. The second polarizer [43] may be further comprised of a combination of polarizer's oriented at different angles to one another. The second polarizer [43] may comprise one of a smaller polarizer in the shape of a small circle [44], and one of a larger polarizer [46] with a small circle cut from the center of the larger polarizer, and wherein the smaller circle polarizer [44] is positioned before the larger polarizer at the location of the small cut circle, or is positioned within the small cut circle of the larger polarizer, and wherein the smaller circle polarizer is oriented at 90 degrees to the first polarizer [41] and larger polarizer is oriented in the same orientation as the first polarizer [41]. The polarizer means may comprises linear polarizers. The polarizer means comprises circular polarizers (or as desired or required).

Example Set No. 2

Referring to the figures throughout, an aspect of an embodiment of the present invention provides a hand-held portable fundus camera system. The hand-held portable fundus camera system may comprise a module optical system [2] capable of being integrated with a consumer camera device [1] for photographing the fundus of an eye [5]. The module optical system [2] may comprise: a composing image acquisition illumination observation source [13] (e.g., photographing light source); a final image acquisition illumination source [12] (e.g. observation light source); and an optical separator and transmitting means [33] (e.g., IR filter [67], heat absorbing glass [31], cold mirror/beam splitter [11]) for separating and transmitting the composing image acquisition observation illumination source [13] and the final image acquisition illumination source [12] to an image mask [10] the image mask [10], of which is relayed to the retina of the fundus [5] through the use of a redirecting mirror [8], a beam splitter [7] and a front converging lens [4]. The module optical system [2] may further comprise: the image mask [10] being configured to provide light that illuminates the retina to output an image that is relayed through the front objective lens [4] and captured by the consumer camera device [1] to provide an image of the retina [5]. The consumer camera device [1] may comprise a consumer point and shoot or digital single lens reflex system (DSLR) module for automated image capture and review. The consumer camera device [1] may further comprise: an external flash device [61]; a hot shoe adapter [3] in communication with the external flash device [61], wherein the captured image being provided by the consumer camera device [1] being in communication with the final image acquisition illumination source [12]. Moreover, the captured image may be properly exposed by the consumer camera device [1] being in communication with the final image acquisition illumination source [12], wherein the external flash device [61] comprises through the lens (TTL) metering to allow the consumer camera device [1] to provide properly exposed images of the retina [5].

Further, the consumer camera device [1] may further comprises at least one of: auto-focusing elements; auto-exposure elements; image stabilization technology; means for taking macro images; LCD for observing the image of the retina; internal flash illumination for enhancing image recorded by the consumer camera; or data storage system for recording of the image of the retina (or any other system, device, composition, material, computer program logic, computer processing, or component as desired or required). The final image acquisition illumination source [12] may be delivered by a transmission channel [63] to the module optical system [2]. The final image acquisition illumination source [12] may be delivered by the transmission channel [63] from the internal flash illumination device [65] of the consumer camera device [1], wherein the transmission channel comprise optical fibers. The final image acquisition illumination source [12] may be delivered by the transmission channel [63] from the external flash illumination source [61] of the consumer camera device [1], wherein the transmission channel comprise optical fibers. The external flash device [61] further comprises a manual slave flash. The manual slave flash further comprises an optical sensor triggered by the internal flash illumination device [65] of the consumer camera device [1]. The manual slave flash further comprises a xenon flash tube separate from the manual slave flash. The xenon flash tube is connected by a transmission channel [63] to the electronics of the manual slave flash, and wherein the transmission channel [63] is an electronic transmission. The electronic transmission channel [63] has a connector to allow detachment from the xenon flash tube. The fundus camera may further comprise a housing [14] that includes the module optical system [2], wherein the xenon flash tube is disposed directly on the fundus camera housing to deliver the final image acquisition illumination source [12]. The external flash device [61] may be further comprised of a through the lens (TTL) metering flash. The external flash illumination device [61] from the through the lens (TTL) metering flash may be configured to be directly controlled by the consumer camera device [1] to control image exposure. The fundus camera may further comprises a hot shoe adapter [3], wherein the use of the consumer camera device [1] is synchronized with the use of the module optical system [2] by means of the hot shoe adapter [3]; and wherein the through the lens (TTL) metering flash is further comprises a connection to the hot shoe adapter [3] to allow control of the external flash illumination device [61] by the consumer camera device [1]. The through the lens (TTL) metering flash may further comprises a xenon flash tube separate from the through the lens (TTL) metering flash. The xenon flash tube may be connected by a transmission channel [63] (e.g., cord or other means as desired or required) to the electronics of the through the lens (TTL) metering flash. The transmission channel [63] (e.g., cord, wire, integrated circuit, circuit, any transmission or communication means, or the like) has a connector to allow detachment from the xenon flash tube. The fundus camera may further comprises a housing [14] that comprises the module optical system [2], wherein the xenon flash tube is disposed directly the fundus camera housing to deliver the final image acquisition illumination source [12]. The xenon flash tube distance to the image mask [10] may be minimized to enhance transmission of flash to allow use of lower power flash for the final image acquisition illumination source [12]. The external flash device [61] my be configured to emit a pre-flash to control image exposure by the consumer camera device [1]. The duration of the pre-flash and the time period between the pre-flash and the final flash emission may be of a duration to prevent pupil constriction prior to the final flash emission. The fundus camera may further comprises a hot shoe adapter [3], wherein the use of the consumer camera device [1] may be synchronized with the use of the module optical system [2] by means of the hot shoe adapter [3]. The hot shoe adapter [3] comprises an electrical connection to the external flash device [61] to provide through the lens (TTL) control of image exposure by the consumer camera device [1].

Example Set No. 3

Referring to the figures throughout, an aspect of an embodiment of the present invention provides a hand-held portable fundus camera system comprising. The hand-held portable fundus camera system may comprise a module optical system [2] capable of being integrated with a consumer camera device [1] for photographing the fundus of an eye [5] using infrared illumination for focusing of the image by the consumer camera device [1]. The module optical system [2] may comprise: a composing image acquisition illumination observation source [13] (e.g., old: photographing light source), wherein the wavelength of the image acquisition illumination source is infrared; a final image acquisition illumination source [12] (e.g., xenon flash tube); and an optical separator and transmitting means [33] (e.g., IR filter [67], heat absorbing glass [31], cold mirror/beam splitter [11]]) for separating and transmitting the composing image acquisition illumination observation source [13] and the final image acquisition illumination source [12] to an image mask [10], of which is relayed to the retina of the fundus through the use of a redirecting mirror [8], a beam splitter [7] and a front objective lens [4]. The module optical system [2] may further comprise the image mask [10] configured to provide light that illuminates the retina to output an image that is relayed through the front objective lens [4] and captured by the consumer camera [1] to provide an image of the retina [5]. The optical separator and transmitting means [33] may further comprise at least one or more of 'a', 'b', or 'c'. Whereby 'a', 'b', or 'c' may include the following: a) separating and transmitting the composing image acquisition illumination observation source [13] that is of infrared wavelengths and the final image acquisition illumination source [12] that is of visible wavelengths; b) separating and transmitting the composing image acquisition illumination observation source [13] that is of visible and infrared wavelengths and the final image acquisition observation illumination source [12] that is of visible and infrared wavelengths; c) separating and transmitting the composing image acquisition illumination observation source [13] that is of visible wavelengths and the final image acquisition illumination source [12] that is of infrared wavelengths. The fundus camera may further comprises of at least one of: an infrared cutoff filter [67] optically disposed between the final image acquisition illumination source [12] and the optical separator and transmitting means [33]; or an infrared cutoff filter [67] optically disposed between the composing image acquisition illumination source [13] and the optical separator and transmitting means [33]. And wherein the consumer camera device [1] may comprise a consumer point and shoot or digital single lens reflex system module for automated image capture and review, whereby an infrared filter has been removed or bypassed from the consumer point and shoot or the digital single lens reflex system module and replaced with a full spectrum filter [69]. The consumer camera device [1] may further comprises: an external flash device [61]; a hot shoe adapter [3] in communication with the external flash device [61], whereby the captured image being provided by the consumer camera device [1] being in communication with the final image acquisition illumination source [12]; and wherein the captured image being properly exposed by the consumer camera device [1] being in communication with the final image acquisition illumination source [12]; and wherein the external flash device [61] comprises through the lens (TTL) metering to allow the consumer camera device [1] to provide properly exposed images of the retina [5].

The infrared cutoff filter [67] may comprises at least one of: an ultraviolet cutoff filter or a visible cutoff filter. The infrared filter may be configured to attenuate infrared wavelength from final image acquisition source is further comprised of at least one of the following: heat absorbing glass; infrared cutoff filter; or cold mirror. The fundus camera may be used for non-dilated (non-mydriatic) photographing of the fundus of an eye. The final illumination acquisition source and the composing image acquisition illumination source may be of different optical paths. The final illumination acquisition source and the composing image acquisition illumination source may be of different power levels enhancing patient comfort during focusing of the fundus camera. The different power levels may be sufficiently different, with the final image acquisition source brighter than the composing image acquisition illumination source, so that shutter speed of the consumer camera device can be set at the speed that results in capture of light from the final image acquisition source with significantly reduced capture of light from the composing image acquisition source without turning off the composing image acquisition source during image capture. The composing image acquisition source may be infrared, but has reduced contribution to the image on the image sensor of the consumer camera device [1] during the image capture by the consumer camera device due to an increased shutter speed determined by a significantly brighter final image acquisition source. The image mask [10] may be configured to create a bundled donut of light. The wherein the module optical system [2] further comprises a rear converging lens [9]; wherein the rear converging lens [9] optically couples an illumination optical path [24] to an imaging acquisition path [23]; wherein the illumination optical path [24] is at first directed parallel to the module imaging acquisition optical path [23]; and wherein the redirecting mirror [8] redirects the illumination optical path so that it is oriented perpendicular to the module imaging optical path. The module illumination optical system [2] may further comprises a diffuser [17]. The module optical system [2] may further comprises a rear converging lens [9]. The rear converging lens optically couples the illumination path [24] to the module imaging acquisition optical path [23]. The distance between the front objective lens the rear converging lens and the image mask may be optimized to reduce back-reflections while still providing adequate illumination of the retina. The size, position, and focal length of the rear converging lens in combination with the front objective lens [4] focuses the bundled donut of light created by the image mask posterior to the cornea. The rear converging lens may be placed between the redirecting mirror [8] and the beam splitter to reduce fundus camera size and increase illumination. The rear converging lens may be placed between the redirecting mirror [8] and the image mask. The composing image acquisition illumination observation light source [13] may comprise a visible light source. The composing image acquisition illumination observation light source [13] may comprise an LED or the like. The LED may comprise a white, red, green, or blue LED or a combination thereof. The blue LED may be a wavelength capable of exciting fluorescein dye for fluorescein angiography. The composing image acquisition illumination observation light source [13] may comprise an infrared light source. The composing image acquisition illumination observation light source [13] may comprises an LED or the like. The LED may comprises a single or multi emitter infrared LED of 850 nm The fundus may further comprise a LED driver [21] (e.g., lighting and timing circuitry or the like) to supply electrical power to the LED. The LED driver [21] may further comprise a boost converter to increase battery voltage to supply electrical power to the LED and a buck converter to supply power from the boost converter to the LED. The final image acquisition illumination source [12] may comprise visible and infrared light sources with means to switch between using the visible light source and the infrared light source. The final image acquisition illumination source [12] may comprise a xenon flash bulb. The final image acquisition illumination source [12] may further comprise a reflector for the xenon flash bulb. The final image acquisition illumination source [12] may further comprise a filter [67] to select a range of wavelengths to transmit in the final image acquisition illumination source [12]. The filter [67] of the final image acquisition illumination source [12] may be an IR cutoff filter or the like. The filter [67] of the final image acquisition illumination source [12] may be a UV cutoff filter. The beam splitter [7] may comprise a standard 50 percent reflection and 50 transmission mirror. The beam splitter [7] may have a spectral range in both visible and infrared spectrum. The beam splitter may comprise a less than 50 percent reflection and greater than 50 percent transmission mirror to enhance transmission of the image of the retina produced by the front objective lens [4] to the consumer camera device [1]. The beam splitter may have a spectral range in both visible and infrared spectrum. The beam splitter [7] may comprise either at least one of dichroic filter, bi-dichroic, triple dichroic, quad dichroic filter, or any combination thereof. The beam splitter being may be configured to transmit infrared wavelengths. The beam splitter may comprise an infrared, red, green, blue quad dichroic. The beamsplitter may be configured to reflect blue light capable of exciting fluorescein dye and transmits the resulting reflected light from the eye to the consumer camera. The beam splitter may comprise an infrared, red, green, blue quad dichroic. The beamsplitter reflects blue light capable of exciting fluorescein dye and transmits the resulting reflected light from the eye to the consumer camera. The module optical system [2] may further comprise a rear converging lens [9], wherein the rear converging lens [9] optically couples an illumination optical path [24] to an imaging acquisition path [23], and wherein the module optical system [2] may further comprise a light trap [6] disposed above the beam splitter [7] whereby light passing through the beam splitter [7] along the illumination optical path [23] and not redirected along the module imaging optical path [24] is absorbed by the light trap [7]. The light trap [6] may be lined with at least one of light absorbing material, black absorbing felt, absorbing neutral density filter, or any combination thereof. The light trap [6] may further comprise walls which cause light to reflect internally within the light trap [6]. The fundus camera may further comprise a housing [14] that includes the module optical system [2] and may be configured to couple the module optical system [2] to the consumer camera device [1]. The housing may be configured to allow detachment from the consumer camera device [1] to enhance manufacturability and maintenance of the fundus camera. The housing [14] may further comprise electrical circuitry [21] to interface the module optical system [2] with the consumer camera [1]. The housing may further comprise a battery-based power source [20] or the like. The housing [14] may be in communication with the module interface system [15], having a mount for the front camera device lens [35] of the consumer camera device [1] to maintain the front camera device lens [35] at a constant focal distance for focusing on the image of the retina produced by the front objective lens [4]. The fundus camera may comprise the housing [14] that comprises the module optical system [2]; a module interface system [15] (e.g. macro lenses, physical coupling, macro extension ring) to integrate the module optical system [2] with the consumer camera device [1]; and wherein the housing [14] provides an optical barrier that separates the illumination path [24] from the module imaging acquisition optical path [23], except between the beamsplitter [7] and the redirecting mirror [8] of the illumination optical path [24]. The housing may be configured to allow detachment of the module illumination path [24] from the image acquisition path [23] to enhance manufacturability and maintenance of the fundus camera. The module interface system [15] may further comprise a macro extension lens [37] to enhance the consumer camera device [1] ability to focus on the image of the retina produced by the consumer camera device [1]. The consumer camera device [1] may comprise a front camera device lens [35], wherein the macro extension ring is positioned to place the central focal point of the camera device front lens [35] at the location of the image formed by the front objective lens [4] for enhancing ability of the consumer camera device [1] to use its entire focal range both positive and negative to allow it to focus on subjects with a range of eyeglass prescriptions. The module interface system [15] may further comprise a macro lens to enhance the consumer camera device's ability to focus on the image of the retina produced by the consumer digital camera device [1]. The consumer camera device [1] may comprise a front camera device lens [35], wherein the macro lens can be positioned to place the central focal point of the camera device front lens [35] at the location of the image formed by the front objective lens [4] for enhancing ability of the consumer camera device [1] to use its entire focal range both positive and negative to allow it to focus on subjects with a range of eyeglass prescriptions. The interface system [15] further comprises a macro extension ring, whereby the macro extension ring being integrated into the housing [14] of the fundus camera to enhance manufacturability of the fundus camera. The image sensor [53] of the consumer camera device [1] may be of a reduced size to increase depth of field of the fundus camera to enhance the range of subject's refractions over which the fundus camera can focus to reduce the need for a manual diopter adjustment. The consumer camera device [1] may further comprises at least one of: auto-focusing elements; auto-exposure elements; image stabilization technology; means for taking macro images; image sensor sensitivity to infrared light through removal of infrared filter in the consumer camera device [1] and replacement with filter that transmits infrared light; LCD for observing the image of the retina; flash illumination for enhancing image recorded by the consumer camera; data storage system for recording of the image of the retina; or a custom mode for storing camera configuration to enhance ease of use for fundus photography (or any other component as provided, desired or required). The data storage system may further comprise a flash memory device (or other storage as desired or required) for storing images of the fundus. The fundus camera may further comprise a transmission module (or any transmission means, circuit or channel as desired or required) for communication to a local and/or remote location. The transmission module may further comprise a network enabled wireless data transfer system with means for transferring recorded images of the fundus [5] to an independent archival system (or other designated, required or desired location or destination). The transmission module may further comprise a combination data storage device and wireless data transfer system. The combination data storage device and wireless data transfer system may further comprise an Eye-fi card or the like. The local and/or remote location is at least one of a user, a processor, a display, a database, an archive, or any combination thereof. The transmission module may provide a means for the communication of images of the fundus to be reviewed by ophthalmologists or care provider in a remote location. The fundus camera may further comprising an LCD screen (or any type of display or graphics). The LCD screen [51] may be configured to show a live image of the image on an image sensor [51] of the consumer camera device [1]. The LCD screen [51] may be a flip screen type that may comprise a rotation mechanism configured to allow inversion of horizontal and vertical axes of the flip screen LCD. The flip screen [51] may further comprise capability to display a mirror image display of the image on the image sensor [53] of the consumer camera device [1] to enhance ease of alignment of camera with the patients eye. The fundus camera according may further comprise an image processing module [55], wherein the consumer camera device comprising an image sensor [53] whereby the image processing module [55] may be configured to enhance the image of the retina recorded by the image sensor [53] of the consumer camera device [1]. The image processing module [55] may be configured to display a mirror image of the image of the retina on the image sensor [53] of the consumer camera device [1]. The image processing module [55] may be configured to separate the spectral wavelength content of the image of the retina recorded by the image sensor [53] of the consumer camera device [1]. The image processing module [55] may further comprise a method for subtracting infrared spectral wavelength content of the image of the retina recorded by the image sensor of the consumer camera device to produce a resultant image that comprises a subset of the spectral content of the image of the retina recorded by the image sensor [53] of the consumer camera device [1]. The subset of the spectral content may further comprise at least one of: red free spectral content; infrared spectral content; ultraviolet spectral content; or visible spectral content. The image processing module [55] may be configured to eliminate back light reflections from the image of the retina recorded by the image sensor [53] of the consumer camera device [1]. The elimination of back light reflections identifies the back light reflections from the retinal image recorded by the image sensor [53] of the consumer camera device [1] by comparing the optical properties of the back light reflections with the optical properties of the retinal image. The optical properties may include at least one of spectral content, size, brightness, or contrast. The image processing module [55] may be configured to subtract the optical properties of the back light reflections with the optical properties of the retinal image to remove the back light reflections and restore the retinal image that is obscured by the back light reflections. The image processing module [55] may be configured to combine overlapping images of the retina recorded by the consumer camera device [1], wherein the back reflection is removed from the final combined image by choosing areas of each individual image that do not include the optical properties of the back reflections. The image processing module [55] may be configured to store a mirror image of the image from the image sensor [53] of the consumer camera device [1] to correct the inverted orientation of the image from the image sensor of the consumer camera device [1]. The image processing module [55] may be configured to adjust the exposure of the recorded image of the consumer camera device [1] to even the illumination across the image recorded of the consumer camera device [1]. The fundus camera according to claim 91, wherein the front objective lens [4] further comprises a multiple element lens. The front objective lens [4] may be a single element lens. The single element lens may comprises at least one of the following: a double aspheric lens; an aspheric convex lens; a convex-convex lens; or a convex-plano lens (or other lens as desired or required). The front objective lens [4] may comprise anti-reflection coatings to reduce illumination source reflections. The front objective lens [4] may be secured by a lens mount [59] with a front converging lens mask to that may be configured to reduce edge image artifacts from the front objective lens [4]. The front objective lens [4] may be a standard lens normally used for indirect ophthalmoscopy. The front objective lens [4] may have an effective power of about 20D to about 22D (e.g., Volk Digital Clearfield lens or an Ocular Instruments OI-22M lens) to provide about 50° field of view of the fundus [5]. The fundus camera according may further comprise a polarizer means, device or system for polarizing light to reduce back light reflections from the fundus camera [2]. The polarizer means comprising a first polarizer [41] may be placed in the image illumination optical path [24] and a second polarizer [43] may be placed in the image acquisition optical path [23]. The first polarizer [41] and/or the second polarizer [43] may be film polarizer type. The first polarizer [42] and/or the second polarizer [43] may be wire grid polarizer type. The first polarizer [41] and/or the second polarizer [43] may be oriented at different angles relative to one another. The first polarizer [41] and/or the second polarizers [43] may be oriented at about 90 degrees to one another to enhance cross polarization to reduce back light reflections from the fundus camera. The first polarizer [41] and/or the second polarizer [43] may be placed after the image mask [10] and between the beamsplitter [7] and front lens [35] of the consumer camera device [2]. The second polarizer [43] may comprise a circle [44] of dimensions needed to cross polarize only the reflection from the front objective lens [4] to reduce back light reflections from the front objective lens [4]. The second polarizer [43] may further comprise a combination of polarizer's oriented at different angles relative to one another. The second polarizer [43] may comprise one of a smaller polarizer in the shape of a small circle [44], and one of a larger polarizer [46] with a small circle cut from the center of the larger polarizer, wherein the smaller circle polarizer [44] may be positioned before the larger polarizer at the location of the small cut circle, or is positioned within the small cut circle of the larger polarizer, and wherein the smaller circle polarizer may be oriented at about 90 degrees to the first polarizer [41] and larger polarizer is oriented in the same orientation as the first polarizer [41]. The polarizer means may comprise a linear polarizer (or other type as desired or required). The polarizer means may comprise circular polarizers.

The devices, systems, devices, compositions, computer program products, and methods of various embodiments of the invention disclosed herein may utilize aspects disclosed in the following references, applications, publications and patents and which are hereby incorporated by reference herein in their entirety:

1. U.S. Pat. No. 5,543,865, Nanjo, T., "Fundus Camera with Partially Common Coaxial Observation and Photographing Optical Systems", Aug. 6, 1996.

2. U.S. Pat. No. 5,668,865, Duttweiler, et al., "Echo Canceler E-Side Speech Detector", Sep. 16, 1997.

3. International Patent Application Publication No. WO 2009/098516 A2, Adrian, P., "Camera Adapter Based Optical Imaging Apparatus", Aug. 13, 2009.

4. U.S. Pat. No. 7,048,379 B2, Miller, et al., "Imaging Lens and Illumination System", May 23, 2006.

5. U.S. Pat. No. 4,266,861, Sawa, S., "Eye Fundus Camera", May 12, 1981.

6. U.S. Patent Application Publication No. US 2008/0231803 A1, Feldon, et al., "Compact Ocular Fundus Camera", Sep. 25, 2008.

7. U.S. Pat. No. 6,546,198 B2, Ohtsuka, H., "Fundus Camera for Diagnostic Fundus Photographing", Apr. 8, 2003.

8. U.S. Pat. No. 7,364,297 B2, Goldfain, et al., "Digital Documenting Ophthalmoscope", Apr. 29, 2008.

9. European Patent Application Publication No. EP 1 354 551 A1, Sugino, et al., "Ophthalmologic Photographing Apparatus, Oct. 22, 2003.

10. U.S. Patent Application Publication No. US 2009/0201467 A1, Smith, et al., "Fundus Photo-Stimulation System and Method", Aug. 13, 2009.

11. U.S. Pat. No. 4,257,688, Matsumura, I., "Eye Examining Instrument", Mar. 24, 1981.

12. U.S. Pat. No. 5,764,341, Fujieda, et al., "Ophthalmic Apparatus", Jun. 9, 1998.

13. U.S. Pat. No. 7,118,218 B2, "Barker, et al., "Method and Device for Imaging a Section of the Eyeground", Oct. 10, 2006.

14. U.S. Pat. No. 7,481,534 B2, Fink, W., "Optomechanical and Digital Ocular Sensor Reader Systems", Jan. 27, 2009.

15. Chalam, K., et al., "Evaluation of Modified Portable Digital Camera for Screening of Diabetic Retinopathy", Ophthalmic Res. 2009; 41:60-62.

16. International Patent Application Publication No. WO 2006/013579 A1, Gupta, S., "A Retinal or Fundus Camera", Feb. 9, 2006.

17. International Patent Application Publication No. WO 2006/086269 A2, Collins, C., et al., "Hand Held Device and Methods for Examining a Patient's Retina", Aug. 17, 2006 (International Application No. PCT/US2006/004031, filed Feb. 6, 2006).

18. International Patent Application Serial No. PCT/US2010/033875, entitled "Self-Illuminated Handheld Lens for Retinal Examination and Photography and Related Method Thereof," filed May 6, 2010.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of embodiments of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A hand-held portable fundus camera system comprising:
a module optical system capable of being integrated with a consumer camera device for auto focus photography by said consumer camera device of the fundus of an eye;
said module optical system, comprising:
a composing image acquisition illumination observation source;
a final image acquisition illumination source;
an optical separator and transmitter for separating and transmitting said composing image acquisition observation illumination source and said final image acquisition illumination source to an image mask, each of which is relayed to the retina of the fundus through the use of a rear converging lens, redirecting mirror, a beam splitter and a front objective lens;
said image mask configured to provide light that illuminates the retina to output an image that is relayed through said objective lens and captured by said consumer camera to provide an image of the retina;
a module interface system to integrate said module optical system with said consumer camera device;
wherein said module interface system enhances the macro focusing capability of said consumer camera device to enable auto-focus photography by said consumer camera device of the fundus image produced by said front objective lens.

2. The fundus camera according to claim 1, wherein said image mask is configured to create a bundled donut of light.

3. The fundus camera according to claim 1, wherein said module optical system further comprises a diffuser.

4. The fundus camera according to claim 1, wherein said rear converging lens optically couples an illumination optical path to an imaging acquisition path.

5. The fundus camera according to claim 4, wherein said module optical system further comprises a light trap disposed above said beam splitter whereby light passing through said beam splitter along said illumination optical path and not redirected along said module imaging optical path is absorbed by said light trap.

6. The fundus camera according to claim 5, wherein said light trap is lined with at least one of light absorbing material, black absorbing felt, absorbing neutral density filter, or any combination thereof.

7. The fundus camera according to claim 5, wherein said light trap further comprises walls which cause light to reflect internally within said light trap.

8. The fundus camera according to claim 4, further comprises a housing that comprises said module optical system and configured to couple said module optical system to said consumer camera device;
wherein said housing provides an optical barrier that separates said illumination optical path from said imaging acquisition optical path except between said beam splitter and said redirecting mirror of said illumination optical path.

9. The fundus camera according to claim 8, wherein said housing allows detachment of said illumination optical path from said imaging acquisition optical path to enhance manufacturability and maintenance of said fundus camera.

10. The fundus camera according to claim 1, wherein distance between said front objective lens and said rear converging lens and said image mask is optimized to reduce back-reflections while still providing adequate illumination of the retina.

11. The fundus camera according to claim 10, wherein the size, position, and focal length of said rear converging lens in combination with said front objective lens focuses the bundled donut of light created by the image mask posterior to the cornea.

12. The fundus camera according to claim 1, wherein said composing image acquisition illumination observation light source comprises a visible light source.

13. The fundus camera according to claim 12, wherein said visible light source comprises an LED.

14. The fundus camera according to claim 12, wherein said visible light source comprises a white, red, green, or blue LED or a combination thereof.

15. The fundus camera according to claim 14, wherein said blue LED provides a wavelength capable of exciting fluorescein dye for fluorescein angiography.

16. The fundus camera according to claim 1, wherein said final image acquisition illumination source comprises a xenon flash bulb.

17. The fundus camera according to claim 16, wherein said final image acquisition source further comprises a reflector for said xenon flash bulb.

18. The fundus camera according to claim 1, wherein said beam splitter comprises a standard 50 percent reflection and 50 transmission mirror.

19. The fundus camera according to claim 1, wherein said beam splitter comprises a less than 50 percent reflection and greater than 50 percent transmission mirror to enhance transmission of the image of the retina produced by said front objective lens to said consumer camera device.

20. The fundus camera according to claim 1, wherein said beam splitter comprises either at least one of dichroic filter, bi-dichroic, or triple dichroic filter, or any combination thereof.

21. The fundus camera according to claim 1, wherein said beam splitter comprises a red, green, blue triple dichroic.

22. The fundus camera according to claim 21, wherein said beamsplitter reflects blue light configured for exciting fluorescein dye and transmits the resulting reflected light from the eye to said consumer camera device.

23. The fundus camera according to claim 1, further comprises a housing that comprises said module optical system and configured to couple said module optical system to said consumer camera device.

24. The fundus camera according to claim 23, wherein said housing further comprises electrical circuitry to interface said module optical system with said consumer camera device.

25. The fundus camera according to claim 23, wherein said housing further comprises a battery-based power source.

26. The fundus camera according to claim 23, wherein said housing in communication with said module interface system, having a mount for the front camera device lens of said consumer camera device to maintain said front camera device lens at a constant focal distance for focusing on said image of the retina produced by said front objective lens.

27. The fundus camera according to claim 23, wherein:
said module interface system further comprises a macro extension ring, said macro extension ring being integrated into said housing of said fundus camera (to enhance manufacturability of said fundus camera).

28. The fundus camera according claim 1, wherein said module interface system further comprises a macro lens and/or a macro extension to enhance said consumer camera device's ability to focus on said image of the retina produced by said consumer camera device.

29. The fundus camera according to claim 28, wherein:
said consumer camera device comprising a front camera device lens;
wherein said macro extension ring is positioned to place the central focal point of said camera device front lens at the location of the image formed by said front objective lens (enhancing ability of said consumer camera to use its entire focal range both positive and negative to allow it to focus on patients with a range of eyeglass prescriptions).

30. The fundus camera according to claim 1, wherein said module interface system further comprises a macro lens to enhance said consumer camera device's ability to focus on said image of the retina produced by said consumer digital camera device.

31. The fundus camera according to claim 30, wherein:
said consumer camera device comprising a front camera device lens;
wherein said macro lens is positioned to place the central focal point of said camera device front lens at the location of the image formed by said front objective lens (enhancing ability of said consumer camera to use its entire focal range both positive and negative to allow it to focus on patients with a range of eyeglass prescriptions).

32. The fundus camera according to claim 1, wherein said consumer camera device further comprises at least one of:
auto-focusing elements;
auto-exposure elements;
image stabilization technology;
means for taking macro images;
LCD for observing said image of the retina;
flash illumination for enhancing image recorded by said consumer camera; or
data storage system for recording of said image of the retina.

33. The fundus camera according to claim 32, wherein said data storage system further comprises a flash memory device for storing images of the fundus.

34. The fundus camera according to claim 1, further comprising a transmission module for communication to a local and/or remote location.

35. The fundus camera according to claim 34, wherein said transmission module further comprises a network enabled wireless data transfer system with means for transferring recorded images of the fundus to an independent archival system.

36. The fundus camera according to claim 35, wherein said transmission module further comprises a combination data storage device and wireless data transfer system.

37. The fundus camera according to claim 36, wherein said combination data storage device and wireless data transfer system further comprises an Eye-fi card.

38. The fundus camera according to claim 34, wherein said local and/or remote location is at least one of a user, a processor, a display, a database, an archive, or any combination thereof.

39. The fundus camera according to claim 34, wherein said transmission module provides means for the communication of images of the fundus to be reviewed by ophthalmologists or care provider in a remote location.

40. The fundus camera according to claim 1, further comprising an LCD screen, said LCD screen configured to show a live image of the image on an image sensor of said consumer camera device.

41. The fundus camera according to claim 40, wherein said LCD screen is a flip screen type comprising a rotation mechanism configured to allow inversion of horizontal and vertical axes of said flip screen LCD.

42. The fundus camera according to claim 40, wherein said flip screen further comprises capability to display a mirror image display of the image on said image sensor of said consumer camera device to enhance ease of alignment of camera with the patients eye.

43. The fundus camera according to claim 1, further comprising an image processing module;
wherein said consumer camera device comprising an image sensor;

said image processing module configured to enhance the image of the retina recorded by said image sensor of said consumer camera device.

44. The fundus camera according to claim 43, wherein said image processing module being configured to display a mirror image of the image of the retina on said image sensor of said consumer camera device.

45. The fundus camera according to claim 43, wherein said image processing module being configured to eliminate back light reflections from said image of the retina recorded by the image sensor of said consumer camera device.

46. The fundus camera according to claim 45, wherein said elimination of back light reflections identifies said back light reflections from the retinal image recorded by said image sensor of said consumer camera device by comparing the optical properties of said back light reflections with the optical properties of the retinal image.

47. The fundus camera according to claim 46, wherein said optical properties include spectral content, size, brightness, and contrast.

48. The fundus camera according to claim 46, wherein said image processing module being configured to subtract said optical properties of said back light reflections with the optical properties of the retinal image to remove said back light reflections and restore said retinal image that is obscured by said back light reflections.

49. The fundus camera according to claim 46, wherein said image processing module being configured to combine overlapping images of the retina recorded by said consumer camera device, wherein the back reflection is removed from the final combined image by choosing areas of each individual image that do not include said optical properties of said back reflections.

50. The fundus camera according to claim 43, wherein said image processing module being configured to store a mirror image of the image from said image sensor of said consumer camera device to correct the inverted orientation of said image from said image sensor of said consumer camera device.

51. The fundus camera according to claim 50, wherein said image processing module being configured to adjust the exposure of said recorded image of said consumer camera device to even the illumination across the image recorded of said consumer camera device.

52. The fundus camera according to claim 1, wherein said front objective lens is a double aspheric lens, an aspheric convex lens, a convex-convex lens, or a convex-piano lens.

53. The fundus camera according to claim 1, wherein said front objective lens has antireflection coatings to reduce illumination source reflections.

54. The fundus camera according to claim 1, wherein said front objective lens is a standard lens normally used for indirect ophthalmoscopy.

55. The fundus camera according to claim 1, wherein said front objective lens has an effective power of about 20D to about 22D to provide about 50° field of view of the fundus.

56. The fundus camera according to claim 1, wherein said front objective lens is secured by a lens mount with a front converging lens mask that is configured to reduce edge image artifacts from said front objective lens.

57. The fundus camera according to claim 1, further comprising a polarizer means for polarizing light to reduce back light reflections from said fundus camera.

58. The fundus camera according to claim 57, wherein said polarizer comprising a first polarizer placed in the illumination optical path and a second polarizer placed in the image acquisition optical path.

59. The fundus camera according to claim 58, wherein said first polarizer and said second polarizer are oriented at different angles relative to one another.

60. The fundus camera according to claim 58, wherein said first polarizer and said second polarizer are oriented at about 90 degrees to one another to enhance cross polarization to reduce back light reflections from said fundus camera.

61. The fundus camera according to claim 60, wherein said first polarizer and said second polarizer are placed after the image mask and between said beamsplitter and said front lens of said consumer camera device.

62. The fundus camera according to claim 58, wherein said second polarizer comprises a circle of dimensions needed to cross polarize only the reflection from said front objective lens to reduce back light reflections from said front objective lens.

63. The fundus camera according to claim 62, wherein said second polarizer is further comprised of a combination of polarizer's oriented at different angles to one another.

64. The fundus camera according to claim 63, wherein:
said second polarizer comprises one of a smaller polarizer in the shape of a small circle,
and one of a larger polarizer with a small circle cut from the center of said larger polarizer,
wherein said smaller circle polarizer is positioned before said larger polarizer at the location of said small cut circle, or is positioned within the small cut circle of said larger polarizer, and
wherein said smaller circle polarizer is oriented at 90 degrees to said first polarizer and larger polarizer is oriented in the same orientation as said first polarizer.

65. The fundus camera according to claim 57, wherein said polarizer comprises at least one linear polarizer.

66. The fundus camera according to claim 57, wherein said polarizer means comprises at least one circular polarizer.

67. A hand-held portable fundus camera system comprising:
a module optical system capable of being integrated with a consumer camera device for photographing the fundus of an eye;
said module optical system, comprising:
a composing image acquisition illumination observation source;
a final image acquisition illumination source;
an optical separator and transmitter for separating and transmitting said composing image acquisition observation illumination source and said final image acquisition illumination source to an image mask, each of which is relayed to the retina of the fundus through the use of a rear converging lens, redirecting mirror, a beam splitter and a front converging lens;
said image mask configured to provide light that illuminates the retina to output an image that is relayed through said front objective lens and captured by said consumer camera device to provide an image of the retina;
wherein said consumer camera device comprises a consumer point and shoot or digital single lens reflex system (DSLR) module for automated image capture and review;
wherein said consumer camera device further comprises:
an external flash device;
a hot shoe adapter in communication with said external flash device,
wherein said captured image being provided by said consumer camera device being in communication with said final image acquisition illumination source;

wherein said captured image being properly exposed by said consumer camera device being in communication with said final image acquisition illumination source;

wherein said external flash device comprises through the lens (TTL) metering to allow said consumer camera device to provide properly exposed images of the retina.

68. The fundus camera according to claim 67, wherein said consumer camera device further comprises at least one of:
   auto-focusing elements;
   auto-exposure elements;
   image stabilization technology;
   means for taking macro images;
   LCD for observing said image of the retina;
   internal flash illumination for enhancing image recorded by said consumer camera; or
   data storage system for recording of said image of the retina.

69. The fundus camera according to any one of claim 67 or 68, wherein said final image acquisition illumination source is delivered by a transmission channel to said module optical system.

70. The fundus camera according to claim 69, wherein said final image acquisition illumination source is delivered by said transmission channel from said internal flash illumination device of said consumer camera device, wherein said transmission channel comprise optical fibers.

71. The fundus camera according to claim 69, wherein said final image acquisition illumination source is delivered by said transmission channel from said external flash illumination source of said consumer camera device, wherein said transmission channel comprise optical fibers.

72. The fundus camera according to anyone of claim 67 or 68, wherein said external flash device further comprises a manual slave flash.

73. The fundus camera according to claim 72, wherein said manual slave flash further comprises an optical sensor triggered by said internal flash illumination device of said consumer camera device.

74. The fundus camera according to claim 72, wherein said manual slave flash further comprises a xenon flash tube separate from said manual slave flash.

75. The fundus camera according to claim 74, wherein said xenon flash tube is connected by a transmission channel to the electronics of said manual slave flash, and wherein said transmission channel is an electronic transmission.

76. The fundus camera according to claim 75, wherein said electronic transmission channel has a connector to allow detachment from said xenon flash tube.

77. The fundus camera according to claim 74, further comprises a housing that comprises said module optical system, wherein said xenon flash tube is disposed directly on said fundus camera housing to deliver said final image acquisition illumination source.

78. The fundus camera according to anyone of claim 67 or 68, wherein said external flash device is further comprised of a through the lens (TTL) metering flash.

79. The fundus camera according to claim 78, wherein said external flash illumination device from said through the lens (TTL) metering flash is configured to be directly controlled by said consumer camera device to control image exposure.

80. The fundus camera according to claim 78, further comprises:
   a hot shoe adapter, wherein the use of said consumer camera device is synchronized with the use of said module optical system by means of said hot shoe adapter; and
   wherein said through the lens (TTL) metering flash is further comprises a connection to said hot shoe adapter to allow control of said external flash illumination device by said consumer camera device.

81. The fundus camera according to claim 80, wherein said through the lens (TTL) metering flash further comprises a xenon flash tube separate from said through said lens (TTL) metering flash.

82. The fundus camera according to claim 81, wherein said xenon flash tube is connected by a transmission channel to the electronics of said through the lens (TTL) metering flash.

83. The fundus camera according to claim 82, wherein said transmission channel has a connector to allow detachment from said xenon flash tube.

84. The fundus camera according to claim 81, further comprises a housing that comprises said module optical system, wherein said xenon flash tube is disposed directly the fundus camera housing to deliver said final image acquisition illumination source.

85. The fundus camera according to claim 84, wherein said xenon flash tube distance to said image mask is minimized to enhance transmission of flash to allow use of lower power flash for said final image acquisition illumination source.

86. The fundus camera according to claim 78, wherein said external flash device emits a pre-flash to control image exposure by said consumer camera device.

87. The fundus camera according to claim 86, where the duration of said pre-flash and the time period between said pre-flash and said final flash emission are of a duration to prevent pupil constriction prior to said final flash emission.

88. The fundus camera according to claim 67, further comprises a hot shoe adapter, wherein the use of said consumer camera device is synchronized with the use of said module optical system by means of said hot shoe adapter.

89. The fundus camera according to claim 88, wherein said hot shoe adapter comprises an electrical connection to said external flash device to provide through the lens (TTL) control of image exposure by said consumer camera device.

90. A hand-held portable fundus camera system comprising:
   a module optical system capable of being integrated with a consumer camera device for photographing the fundus of an eye using infrared illumination for focusing of the image by said consumer camera device;
   said module optical system, comprising:
      a composing image acquisition illumination observation source, wherein the wavelength of said image acquisition illumination source is infrared;
      a final image acquisition illumination source;
      an optical separator and transmitter for separating and transmitting said composing image acquisition illumination observation source and said final image acquisition illumination source to an image mask, each of which is relayed to the retina of the fundus through the use of a rear converging lens, redirecting mirror, a beam splitter and a front objective lens;
      said image mask configured to provide light that illuminates the retina to output an image that is relayed through said front objective lens and captured by said consumer camera to provide an image of the retina;
      wherein said optical separator and transmitter further comprises at least one or more of 'a', 'b', or 'c':
         a) separating and transmitting said composing image acquisition illumination observation source that is of infrared wavelengths and said final image acquisition illumination source that is of visible wavelengths;

b) separating and transmitting said composing image acquisition illumination observation source that is of visible and infrared wavelengths and said final image acquisition observation illumination source that is of visible and infrared wavelengths;
c) separating and transmitting said composing image acquisition illumination observation source that is of visible wavelengths and said final image acquisition illumination source that is of infrared wavelengths;
wherein said fundus camera further comprises of at least one of:
an infrared cutoff filter optically disposed between said final image acquisition illumination source and said optical separator and transmitter;
an infrared cutoff filter optically disposed between said composing image acquisition illumination source and said optical separator and transmitter;
wherein said consumer camera device comprises a consumer point and shoot or digital single lens reflex system module for automated image capture and review;
wherein an infrared filter has been removed or bypassed from said consumer point and shoot or said digital single lens reflex system module and replaced with a full spectrum filter;
wherein said consumer camera device further comprises:
an external flash device;
a hot shoe adapter in communication with said external flash device;
wherein said captured image being provided by said consumer camera device being in communication with said final image acquisition illumination source;
wherein said captured image being properly exposed by said consumer camera device being in communication with said final image acquisition illumination source;
wherein said external flash device comprises through the lens (TTL) metering to allow the said consumer camera device to provide properly exposed images of the retina.

91. The fundus camera according to claim 90, wherein: said infrared cutoff filter comprises at least one of: an ultraviolet cutoff filter or a visible cutoff filter.

92. The fundus camera according to claim 90, wherein said infrared filter being configured to attenuate infrared wavelength from final image acquisition source is further comprised of at least one of the following:
heat absorbing glass;
infrared cutoff filter; or
cold mirror.

93. The fundus camera according to claim 90, where said fundus camera is used for non-dilated (non-mydriatic) photographing of the fundus of an eye.

94. The fundus camera according to claim 90, where said final illumination acquisition source and said composing image acquisition illumination source are of different optical paths.

95. The fundus camera according to claim 90, where said final illumination acquisition source and said composing image acquisition illumination source are of different power levels enhancing patient comfort during focusing of said fundus camera.

96. The fundus camera according to claim 95, where said different power levels are sufficiently different, with said final image acquisition source brighter than said composing image acquisition illumination source, so that shutter speed of said consumer camera device can be set at said speed that results in capture of light from said final image acquisition source with significantly reduced capture of light from said composing image acquisition source without turning off said composing image acquisition source during image capture.

97. The fundus camera according to claim 96, where said composing image acquisition source is infrared, but has reduced contribution to the image on the image sensor of said consumer camera device during said image capture by said consumer camera device due to an increased shutter speed determined by a significantly brighter final image acquisition source.

98. The fundus camera according to claim 90, wherein said image mask is configured to create a bundled donut of light.

99. The fundus camera according to claim 90, wherein:
wherein said rear converging lens optically couples an illumination optical path to an imaging acquisition path;
wherein said illumination optical path is at first directed parallel to said module imaging acquisition optical path; and
wherein said redirecting mirror redirects said illumination optical path so that it is oriented perpendicular to said module imaging optical path.

100. The fundus camera according to claim 90, wherein said module illumination optical system further comprises a diffuser.

101. The fundus camera according to claim 90, wherein said rear converging lens optically couples the illumination path to the module imaging acquisition optical path.

102. The fundus camera according to claim 90, wherein distance between said front objective lens said rear converging lens and said image mask is optimized to reduce back-reflections while still providing adequate illumination of the retina.

103. The fundus camera according to claim 90, wherein the size, position, and focal length of said rear converging lens in combination with said front objective lens focuses the bundled donut of light created by the image mask posterior to the cornea.

104. The fundus camera according to claim 90, wherein said rear converging lens is placed between said redirecting mirror and said beam splitter to reduce fundus camera size and increase illumination.

105. The fundus camera according to claim 90, wherein said rear converging lens is placed between said redirecting mirror and said image mask.

106. The fundus camera according to claim 90, wherein said composing image acquisition illumination observation light source comprises a visible light source.

107. The fundus camera according to claim 106, wherein said composing image acquisition illumination observation light source comprises an LED.

108. The fundus camera according to claim 107, wherein said LED comprises a white, red, green, or blue LED or a combination thereof.

109. The fundus camera according to claim 108, wherein the blue LED is a wavelength capable of exciting fluorescein dye for fluorescein angiography.

110. The fundus camera according to claim 90, wherein said composing image acquisition illumination observation light source comprises an infrared light source.

111. The fundus camera according to claim 110, wherein said composing image acquisition illumination observation light source comprises an LED.

112. The fundus camera according to claim 111, wherein said LED comprises a single or multi emitter infrared LED of 850 nm.

113. The fundus camera according to claim 112, further comprises a LED driver to supply electrical power to said LED.

114. The fundus camera according to claim 113, wherein said LED driver further comprises a boost converter to increase battery voltage to supply electrical power to said LED and a buck converter to supply power from said boost converter to said LED.

115. The fundus camera according to claim 90, wherein said final image acquisition illumination source comprises visible and infrared light sources with means to switch between using said visible light source and said infrared light source.

116. The fundus camera according to claim 90, wherein said final image acquisition illumination source comprises a xenon flash bulb.

117. The fundus camera according to claim 116, wherein said final image acquisition illumination source further comprises a reflector for said xenon flash bulb.

118. The fundus camera according to claim 117, wherein said final image acquisition illumination source further comprises a filter to select a range of wavelengths to transmit in said final image acquisition illumination source.

119. The fundus camera according to claim 118, wherein said filter of said final image acquisition illumination source is an IR cutoff filter.

120. The fundus camera according to claim 118, wherein said filter of said final image acquisition illumination source is a UV cutoff filter.

121. The fundus camera according to claim 90, wherein said beam splitter comprises a standard 50 percent reflection and 50 transmission mirror.

122. The fundus camera according to claim 121, wherein said beam splitter has a spectral range in both visible and infrared spectrum.

123. The fundus camera according to claim 90, wherein said beam splitter comprises a less than 50 percent reflection and greater than 50 percent transmission mirror to enhance transmission of the image of the retina produced by said front objective lens to said consumer camera device.

124. The fundus camera according to claim 123, wherein said beam splitter has a spectral range in both visible and infrared spectrum.

125. The fundus camera according to claim 90, wherein said beam splitter comprises either at least one of dichroic filter, bi-dichroic, triple dichroic, quad dichroic filter, or any combination thereof.

126. The fundus camera according to claim 125, wherein said beam splitter being configured to transmit infrared wavelengths.

127. The fundus camera according to claim 126, wherein said beam splitter comprises an infrared, red, green, blue quad dichroic.

128. The fundus camera according to claim 127, wherein said beamsplitter reflects blue light capable of exciting fluorescein dye and transmits the resulting reflected light from the eye to said consumer camera.

129. The fundus camera according to claim 90, wherein said beam splitter comprises an infrared, red, green, blue quad dichroic.

130. The fundus camera according to claim 129, wherein said beamsplitter reflects blue light capable of exciting fluorescein dye and transmits the resulting reflected light from the eye to said consumer camera.

131. The fundus camera according to claim 90, wherein:
said module optical system further comprises a rear converging lens;
said rear converging lens optically couples an illumination optical path to an imaging acquisition path;
said module optical system further comprises a light trap disposed above said beam splitter whereby light passing through said beam splitter along said illumination optical path and not redirected along said module imaging optical path is absorbed by said light trap.

132. The fundus camera according to claim 131, wherein said light trap is lined with at least one of light absorbing material, black absorbing felt, absorbing neutral density filter, or any combination thereof.

133. The fundus camera according to claim 131, wherein said light trap further comprises walls which cause light to reflect internally within said light trap.

134. The fundus camera according to claim 90, further comprises a housing that comprises said module optical system and configured to couple said module optical system to said consumer camera device.

135. The fundus camera according to claim 134, wherein said housing configured to allow detachment from said consumer camera device to enhance manufacturability and maintenance of said fundus camera.

136. The A fundus camera according to claim 134, wherein said housing further comprises electrical circuitry to interface said module optical system with said consumer camera.

137. The fundus camera according to claim 134, wherein said housing further comprises a battery-based power source.

138. The fundus camera according to claim 134, wherein said housing in communication with said module interface system, having a mount for the front camera device lens of said consumer camera device to maintain said front camera device lens at a constant focal distance for focusing on said image of the retina produced by said front objective lens.

139. The fundus camera according to claim 90, further comprises:
a housing that comprises said module optical system;
a module interface system to integrate said module optical system with said consumer camera device; and
wherein said housing provides an optical barrier that separates said illumination path from said module imaging acquisition optical path, except between said beamsplitter and said redirecting mirror of said illumination optical path.

140. The fundus camera according to claim 139, wherein said housing allows detachment of said module illumination path from said image acquisition path to enhance manufacturability and maintenance of said fundus camera.

141. The fundus camera according claim 90, wherein said module interface system further comprises a macro extension lens to enhance said consumer camera device ability to focus on said image of the retina produced by said consumer camera device.

142. The fundus camera according to claim 141, wherein:
said consumer camera device comprising a front camera device lens;
wherein said macro extension ring is positioned to place the central focal point of said camera device front lens at the location of the image formed by said front objective lens for enhancing ability of said consumer camera device to use its entire focal range both positive and negative to allow it to focus on subjects with a range of eyeglass prescriptions.

143. The fundus camera according to claim 141, wherein said module interface system further comprises a macro lens to enhance said consumer camera device's ability to focus on said image of the retina produced by said consumer digital camera device.

144. The fundus camera according to claim 143, wherein:
said consumer camera device comprising a front camera device lens;
wherein said macro lens is positioned to place the central focal point of said camera device front lens at the location of the image formed by said front objective lens for enhancing ability of said consumer camera device to use its entire focal range both positive and negative to allow it to focus on subjects with a range of eyeglass prescriptions.

145. The fundus camera according to claim 141, wherein said module interface system further comprises a macro extension ring 45, said macro extension ring being integrated into said housing of said fundus camera to enhance manufacturability of said fundus camera.

146. The fundus camera according to claim 90, wherein said image sensor of said consumer camera device is of a reduced size to increase depth of field of said fundus camera to enhance the range of subject's refractions over which said fundus camera can focus to reduce the need for a manual diopter adjustment.

147. The fundus camera according to claim 90, wherein said consumer camera device further comprises at least one of:
auto-focusing elements;
auto-exposure elements;
image stabilization technology;
means for taking macro images;
image sensor sensitivity to infrared light through removal of infrared filter in said consumer camera device and replacement with filter that transmits infrared light;
LCD for observing said image of the retina;
flash illumination for enhancing image recorded by said consumer camera;
data storage system for recording of said image of the retina; or
a custom mode for storing camera configuration to enhance ease of use for fundus photography.

148. The fundus camera according to claim 147, wherein said data storage system further comprises a flash memory device for storing images of the fundus.

149. The fundus camera according to claim 90, further comprising a transmission module for communication to a local and/or remote location.

150. The fundus camera according to claim 149, wherein said transmission module further comprises a network enabled wireless data transfer system with means for transferring recorded images of the fundus to an independent archival system.

151. The fundus camera according to claim 149, wherein said transmission module further comprises a combination data storage device and wireless data transfer system.

152. The fundus camera according to claim 151, wherein said combination data storage device and wireless data transfer system further comprises an Eye-fi card.

153. The fundus camera according to claim 149, wherein said local and/or remote location is at least one of a user, a processor, a display, a database, an archive, or any combination thereof.

154. The fundus camera according to claim 149, wherein said transmission module provides means for the communication of images of the fundus to be reviewed by ophthalmologists or care provider in a remote location.

155. The fundus camera according to claim 90, further comprising an LCD screen, said LCD screen configured to show a live image of the image on an image sensor of said consumer camera device.

156. The fundus camera according to claim 155, wherein said LCD screen is a flip screen type comprises rotation mechanism configured to allow inversion of horizontal and vertical axes of said flip screen LCD.

157. The fundus camera according to claim 155, wherein said flip screen further comprises capability to display a mirror image display of the image on said image sensor of said consumer camera device to enhance ease of alignment of camera with the patients eye.

158. The fundus camera according to claim 90, further comprising an image processing module;
wherein said consumer camera device comprising an image sensor;
said image processing module configured to enhance the image of the retina recorded by said image sensor of said consumer camera device.

159. The fundus camera according to claim 158, wherein said image processing module being configured to display a mirror image of the image of the retina on said image sensor of said consumer camera device.

160. The fundus camera according to claim 158, wherein said image processing module being configured to separate the spectral wavelength content of said image of the retina recorded by the image sensor of said consumer camera device.

161. The fundus camera according to claim 160, wherein said image processing module further comprises a method for subtracting infrared spectral wavelength content of said image of the retina recorded by the image sensor of said consumer camera device to produce a resultant image that comprises a subset of said spectral content of said image of the retina recorded by the image sensor of said consumer camera device.

162. The fundus camera according to claim 161, wherein said subset of said spectral content further comprises at least one of:
red free spectral content;
infrared spectral content;
ultraviolet spectral content; or
visible spectral content.

163. The fundus camera according to claim 158, wherein said image processing module being configured to eliminate back light reflections from said image of the retina recorded by the image sensor of said consumer camera device.

164. The fundus camera according to claim 163, wherein said elimination of back light reflections identifies said back light reflections from the retinal image recorded by said image sensor of said consumer camera device by comparing the optical properties of said back light reflections with the optical properties of the retinal image.

165. The fundus camera according to claim 164, wherein said optical properties include at least one of spectral content, size, brightness, or contrast.

166. The fundus camera according to claim 164, wherein said image processing module being configured to subtract said optical properties of said back light reflections with the optical properties of the retinal image to remove said back light reflections and restore said retinal image that is obscured by said back light reflections.

167. The fundus camera according to claim 164, wherein said image processing module being configured to combine overlapping images of the retina recorded by said consumer camera device, wherein the back reflection is removed from the final combined image by choosing areas of each individual image that do not include said optical properties of said back reflections.

168. The fundus camera according to claim 158, wherein said image processing module being configured to store a mirror image of the image from said image sensor of said consumer camera device to correct the inverted orientation of said image from said image sensor of said consumer camera device.

169. The fundus camera according to claim 168, wherein said image processing module being configured to adjust the exposure of said recorded image of said consumer camera device to even the illumination across the image recorded of said consumer camera device.

170. The fundus camera according to claim 90, wherein said front objective lens further comprises a multiple element lens.

171. The fundus camera according to claim 90, wherein said front objective lens is a single element lens.

172. The fundus camera according to claim 171, wherein said single element lens comprises at least one of the following:
 a double aspheric lens;
 an aspheric convex lens;
 a convex-convex lens; or
 a convex-piano lens.

173. The fundus camera according to claim 170, wherein said front objective lens comprises antireflection coatings to reduce illumination source reflections.

174. The fundus camera according to claim 170, wherein said front objective lens is secured by a lens mount with a front converging lens mask to that is configured to reduce edge image artifacts from said front objective lens.

175. The fundus camera according to claim 90, where said front objective lens is a standard lens normally used for indirect ophthalmoscopy.

176. The fundus camera according to claim 90, wherein said front objective lens has an effective power of about 20D to about 22D to provide about 50° field of view of the fundus.

177. The fundus camera according to claim 90, further comprising a polarizer means for polarizing light to reduce back light reflections from said fundus camera.

178. The fundus camera according to claim 177, wherein said polarizer comprising a first polarizer is placed in the image illumination optical path and a second polarizer is placed in the image acquisition optical path.

179. The fundus camera according to claim 178, wherein said first polarizer and/or said second polarizer are film polarizer type.

180. The fundus camera according to claim 178, wherein said first polarizer and/or said second polarizer are wire grid polarizer type.

181. The fundus camera according to claim 178, wherein said first polarizer and/or said second polarizer are oriented at different angles relative to one another.

182. The fundus camera according to claim 178, wherein said first polarizer and/or said second polarizers are oriented at about 90 degrees to one another to enhance cross polarization to reduce back light reflections from said fundus camera.

183. The fundus camera according to claim 182, wherein said first polarizer and/or said second polarizer are placed after said image mask and between said beamsplitter and front lens of said consumer camera device.

184. The fundus camera according to claim 178, wherein the said second polarizer comprises a circle of dimensions needed to cross polarize only the reflection from said front objective lens to reduce back light reflections from said front objective lens.

185. The fundus camera according to claim 184, wherein said second polarizer further comprises of a combination of polarizer's oriented at different angles relative to one another.

186. The fundus camera according to claim 185, wherein:
 said second polarizer comprises one of a smaller polarizer in the shape of a small circle,
 and one of a larger polarizer with a small circle cut from the center of said larger polarizer,
 wherein said smaller circle polarizer is positioned before said larger polarizer at the location of said small cut circle, or is positioned within the small cut circle of said larger polarizer, and
 and wherein said smaller circle polarizer is oriented at 90 degrees to said first polarizer and larger polarizer is oriented in the same orientation as said first polarizer.

187. The fundus camera according to claim 177, wherein said polarizer means comprises a linear polarizer.

188. The fundus camera according to claim 177, wherein said polarizer comprises at least one circular polarizer.

* * * * *